US010067109B2

(12) United States Patent
Frehn et al.

(10) Patent No.: US 10,067,109 B2
(45) Date of Patent: Sep. 4, 2018

(54) METHOD FOR TRACKING HEAT EXPOSURE OF FOODSTUFFS

(71) Applicant: Momentum Machines Company, San Francisco, CA (US)

(72) Inventors: Steven Frehn, San Francisco, CA (US); Alexandros Vardakostas, San Francisco, CA (US)

(73) Assignee: Creator, Inc., San Francisco, CA (US)

( * ) Notice: Subject to any disclaimer, the term of this patent is extended or adjusted under 35 U.S.C. 154(b) by 145 days.

(21) Appl. No.: 15/007,331

(22) Filed: Jan. 27, 2016

(65) Prior Publication Data

US 2016/0213053 A1 Jul. 28, 2016

Related U.S. Application Data

(60) Provisional application No. 62/108,376, filed on Jan. 27, 2015.

(51) Int. Cl.
*G01N 33/02* (2006.01)
*A23P 20/20* (2016.01)
(Continued)

(52) U.S. Cl.
CPC ............... *G01N 33/02* (2013.01); *A23L 5/10* (2016.08); *A23P 20/20* (2016.08); *G01K 1/022* (2013.01); *G01K 2207/04* (2013.01)

(58) Field of Classification Search
CPC .... G01K 13/00; G01K 13/10; G01K 2207/02; G01K 11/00; G01K 1/022;
(Continued)

(56) References Cited

U.S. PATENT DOCUMENTS

2011/0265658 A1* 11/2011 Talon ............... A47J 31/005
99/289 R

FOREIGN PATENT DOCUMENTS

WO WO 2013184910 A1 * 12/2013 ............ A21C 9/04

OTHER PUBLICATIONS

"Temperature Controls of Potentially Hazardous Food." Mar. 30, 2012. California Department of Education. <http://www.cde.ca.gov/ls/nu/sf/mbnsdsfsp012008.asp>. Accessed Aug. 4, 2017.*
(Continued)

*Primary Examiner* — Michele L Jacobson
*Assistant Examiner* — Ericson M Lachica
(74) *Attorney, Agent, or Firm* — Harness, Dickey & Pierce, P.L.C.

(57) ABSTRACT

One variation of a method for tracking temperature exposure of foodstuffs within an automated sandwich assembly apparatus includes: at a topping module, receiving first topping sample and a second topping sample in a column of topping samples; at a first time, determining a first temperature of the first topping sample; in response to the first temperature of the first topping sample exceeding a threshold temperature, setting a first timer assigned to the first topping sample; cutting a slice from the second topping sample; following dispensation of the slice of the second topping sample from the topping module, tracking a position of the first topping sample within the topping module; and in response to expiration of the first timer prior to dispensation of a final portion of the first topping sample from the topping module, disqualifying the final portion of the first topping sample from dispensation onto a topping vehicle.

16 Claims, 7 Drawing Sheets

(51) Int. Cl.
*G01K 1/02* (2006.01)
*A23L 5/10* (2016.01)

(58) Field of Classification Search
CPC .... G01K 2207/04; G01N 33/02; G01N 25/20;
A21C 15/002; G01J 5/60; G01J 5/0003;
G01F 1/7084; A23P 1/086; A23P 20/20;
A23L 1/0067; A23L 5/10
USPC ....................................................... 99/450.4
See application file for complete search history.

(56) References Cited

OTHER PUBLICATIONS

Grinstead, Gale. "Fighting Food Manufacturing Fears: How to Control & Eliminate Listeria." Dec. 11, 2006. <https:www.foodmanufacturing.com/article/2006/12/fighting-food-manufacturing-fears-how-control-eliminate-listeria>. Accessed Aug. 4, 2017.*

"Temperature Mapping Services." Wessex Power. 2010. <http://www.wessexpower.co.uk/services/temperaturemapping/?id=620>. Accessed Sep. 7, 2017.*

"Ending the Great Condiment Debate—Refrigerate?" celeb_2006. Jun. 1, 2011. <http://www.gossiprocks.com/forum/food-cuisine/151883-ending-great-condiment-debate-refrigerate.html>. Accessed Sep. 7, 2017.*

* cited by examiner

METHOD FOR TRACKING HEAT EXPOSURE OF FOODSTUFFS

CROSS-REFERENCE TO RELATED APPLICATIONS

This Application claims the benefit of U.S. Provisional Application No. 62/108,376, filed on 27 Jan. 2015, which is incorporated in its entirety by this reference.

This Application is related to U.S. patent application Ser. No. 14/534,038, filed on 5 Nov. 2014, which is incorporated in its entirety by this reference.

TECHNICAL FIELD

This invention relates generally to the field of food preparation and more specifically to a new and useful method for tracking heat exposure of foodstuffs.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
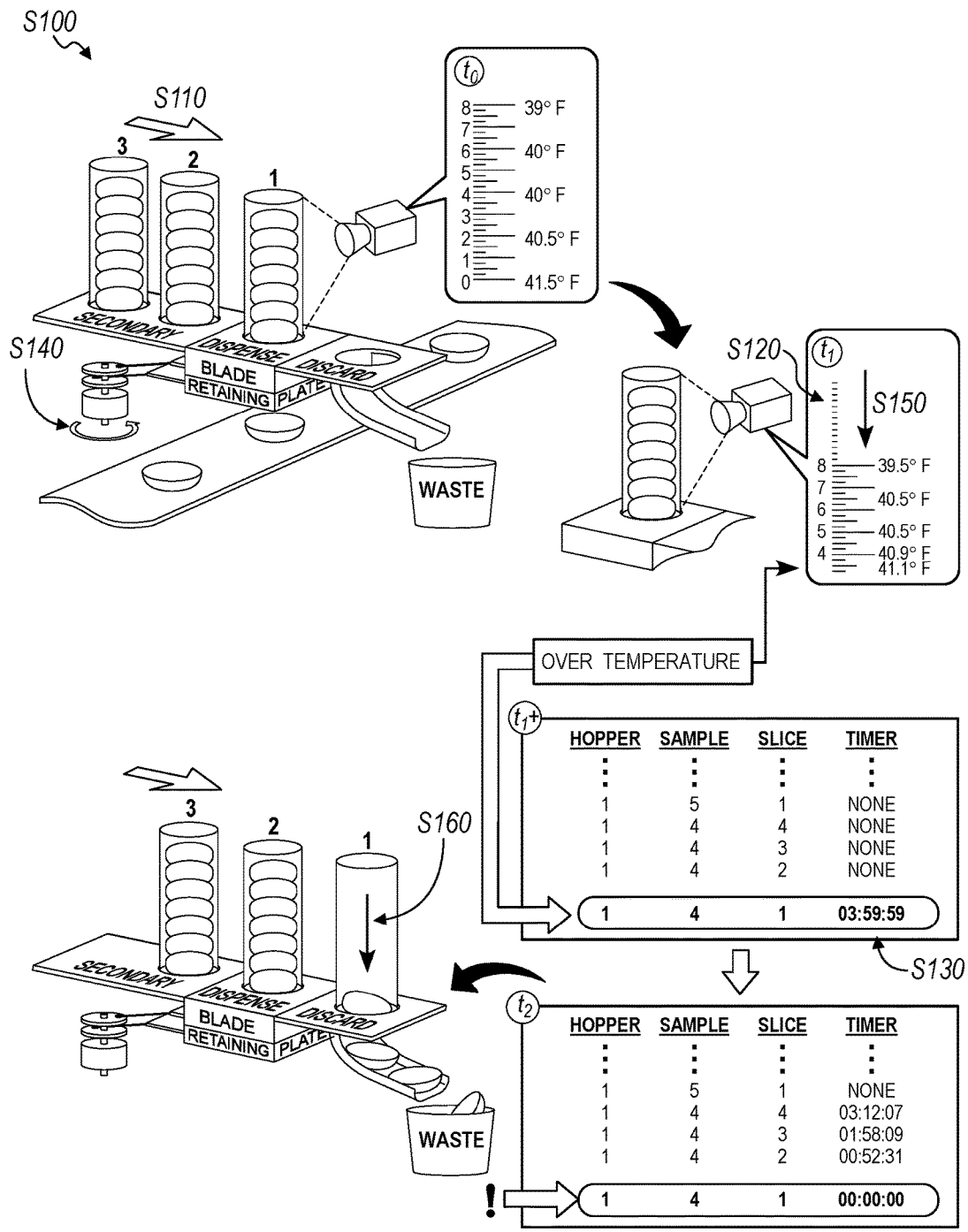
FIG. 1 is a flowchart representation of a method.

As shown in FIG. 1, a method for tracking heat exposure of foodstuffs within an automated sandwich assembly apparatus includes: at a topping module, receiving a column of topping samples including a first topping sample and a second topping sample of a first topping type in Block S110, the second topping sample preceding the first topping sample in the column of topping samples; at a first time, determining a first temperature of the first topping sample in Block S120; in response to the first temperature of the first topping sample exceeding a threshold temperature, setting a first timer assigned to the first topping sample in Block S130; cutting a slice from the second topping sample in Block S140; at a second time succeeding the first time, in response to dispensation of the slice of the second topping sample from the topping module onto a topping vehicle, tracking a position of the first topping sample within the topping module in Block S150; and, in response to expiration of the first timer prior to dispensation of a final portion of the first topping sample from the topping module, disqualifying the final portion of the first topping sample from dispensation onto a topping vehicle in Block S160.

One variation of the method includes: at a topping module, receiving a column of topping samples including a first topping sample and a second topping sample of a first topping type in Block S110, the second topping sample preceding the first topping sample in the column of topping samples; at a first time, determining temperatures along the column of topping samples in Block S120; in response to the particular temperature at a particular position along the column of topping samples exceeding a threshold temperature, setting a timer assigned to the particular position along the column of topping samples in Block S130; proximal a dispense end of the topping module, cutting slice from topping samples below the particular position along the column of topping samples in Block S140; in response to dispensation of slice from the column of topping samples onto topping vehicles, tracking shifts in the particular position along the column of topping samples toward the dispense end of the topping module in Block S150; and in response to expiration of the first timer prior to dispensation of a particular topping sample, coinciding with the particular position along the column of topping samples, from the topping module, disqualifying the particular topping sample from dispensation onto a topping vehicle in Block S160.

Another variation of the method includes: at a first time, measuring a first temperature at a first position within a hopper containing a series of topping samples of a topping type; substantially at the first time, measuring a first temperature at a second position within the hopper above the first position; and estimating a temperature of each topping sample in the series of topping samples in the hopper at the first time based on the first temperature at the first position, the first temperature at the second position, and a position of each topping sample in the series of topping samples in the hopper at the first time in Block S120. In this variation, the method also includes: setting a timer for a first topping sample in the series of topping samples in response to an estimated temperature of the first topping sample exceeding a threshold temperature in Block S130; in response to dispensing a slice of a second topping sample in the series of topping samples from the hopper onto a topping vehicle arranged below the hopper, determining a second position of the first topping sample in the hopper at a second time succeeding the first time in Block S150; and, in response to expiration of the first timer prior to dispensation of a final portion of the first topping sample from the hopper, discarding the final portion of the first topping sample from the hopper in Block S160.

2. Applications

Generally, Blocks of the method can be executed by an automated foodstuff assembly apparatus while assembling a foodstuff (e.g., a sandwich) in order to track heat exposure of topping samples stored in a topping module within the automated foodstuff assembly apparatus, to confirm that a topping sample within the topping module has not been exposed to excess heat before dispensing a slice from the topping sample onto a topping vehicle (e.g., a bread bun), and to identify and disqualify all or portions of topping samples that have been exposed to excess heat. In particular, the automated foodstuff assembly apparatus can implement Blocks of the method: to sample one or more temperature sensors thermally coupled to a hopper arranged within the automated foodstuff assembly apparatus and containing topping samples; to determine temperatures of particular points, segments, topping samples, or clusters of topping samples within the hopper based on outputs of the temperature sensor(s) in Block S120; to set a timer for a point, segment, topping sample, or cluster of topping samples within the hopper if a corresponding temperature exceeds a threshold temperature in Block S130; to dispense a slice from a topping sample onto a topping vehicle below based on a request for the topping type in a food order corresponding to the topping vehicle if the slice of the topping sample is not associated with an expired timer in Block S140; and to actively discard or passively trigger disposal of the corresponding topping sample segment, topping sample, or cluster of topping samples if the timer expires before the topping sample segment, topping sample, or cluster of topping samples is fully dispensed from the hopper.

The automated foodstuff assembly apparatus can execute Blocks of the method to realize food handling requirements and/or to automatically comply with food codes for storing, handling, and serving foodstuffs dispensed from one or more topping modules arranged within the automated foodstuff assembly apparatus. For example, the automated foodstuff assembly apparatus can include a topping module that receives hoppers containing a column of tomatoes with the tops and bottoms of each tomato removed. In this example, because tomatoes in the topping module have been cut, the tomatoes may be subject to particular food handling requirements, such as requirements: to maintain the tomatoes below a temperature of 41° F. before serving; and not serve any tomato that has been exposed to a temperature greater than 41° F. and less than 70° F. for more than four hours; and to not serve any tomato that has been exposed to a temperature greater than 70° F. for more than two hours. Therefore, in this example, the automated foodstuff assembly apparatus can execute Blocks of the method to track temperatures of tomatoes within the hopper, to set timers (e.g., four-hour timers) for tomatoes that have been exposed to temperatures above 41° F. and below 70° F. while stored in the hopper, and to selectively discard (or flag for disposal) tomatoes (or sections of tomatoes) stored in the hopper for which assigned timers have expired in order to comply with food handling requirements for cut tomatoes automatically and in real-time.

The automated foodstuff assembly apparatus is described herein as a system for assembling hamburgers. In particular, the automated foodstuff assembly apparatus is described herein as executing Blocks of the method to dispense slices of topping samples onto topping vehicles including bread buns, such as hamburger bun heels. However, the automated foodstuff assembly apparatus can additionally or alternatively assemble disparate ingredients into sandwiches, hamburgers, hot dogs, wraps, tacos, burritos, salads, crepes, bowls of soup, omelets, and/or any other foodstuff. The automated foodstuff assembly apparatus can therefore dispense slices of topping samples onto topping vehicles including bread slices, hot dog buns, pita, sofa or hard taco shells, etc. The automated foodstuff assembly apparatus can alternatively dispense slices of topping samples onto a conveyor, onto a robotic arm assembly, into a tray, into a box, or onto a topping vehicle of any other form or type. Furthermore, a topping module described herein can execute Blocks of the method independently of an automated foodstuff assembly apparatus. For example, a topping module described herein can function as a standalone system for storing foodstuffs and dispensing foodstuffs, such as a system for storing and dispensing slices of tomatoes, oranges, pickles, strawberries, bread, apples, garlic, cheese, etc. However, any other system, subsystem, foodstuff assembly apparatus, or topping module, etc. can execute Blocks of the method. Blocks of the method can also be executed by a local or remote computer system, such as computer network or remote server.

3. Automated Foodstuff Assembly Apparatus

The automated foodstuff assembly apparatus can include one or more subsystems that cooperate to prepare, portion, and/or dispense disparate components of a hamburger and that cooperate to assemble these disparate components into a completed hamburger. For example, the automated foodstuff assembly system can include a patty grinding subsystem that grinds and presses custom hamburger patties from raw meat (such as based on custom patty orders), a patty grilling subsystem that grills patties (e.g., rare, medium, or well-done patties based on custom patty orders), a bun toaster subsystem that toasts bun crowns and bun heels (e.g., "topping vehicles"), a topping subsystem that loads toppings and condiments onto bun heels (e.g., based on custom topping orders), and a bagging subsystem that loads completed hamburgers into paper bags for delivery to patrons. In this example, the automated foodstuff assembly system can function as a vending machine installed within a restaurant, within a retail space, within a corporate space, within a convention, etc. to automatically assemble custom hamburgers based on orders received from patrons and to supply these completed custom hamburgers for pickup and substantially immediate consumption by their corresponding patrons.

In one implementation, the automated foodstuff assembly apparatus includes five topping modules, wherein each topping module dispenses one of lettuce, tomato, onion, pickle, and avocado (i.e., topping samples) into a bowl to create a salad, onto a bun to assemble a hamburger, and/or onto a slice of bread to assemble a sandwich. In this implementation, a lettuce topping module can be loaded with coarsely-chopped lettuce, a tomato topping module can be loaded with a column of tomatoes with their tops and bottoms cut flat, an onion topping module can be loaded with a column of peeled onions with their tops and bottoms cut flat, a pickle topping module can be loaded with three columns of pickles with their tops and bottoms cut flat, and an avocado topping module can be loaded with sections of avocado with skin and pit removed. In this example, select topping modules can be loaded with topping samples with their tops and bottoms cut flat such that slices cut from these topping samples and dispensed onto topping vehicles exhibit substantially uniform thickness, and other topping modules can be loaded with trimmed, peeled, or otherwise cut topping samples. Because these topping modules are loaded with cut topping samples that may be subject to temperature exposure requirements, the automated foodstuff assembly apparatus can track temperatures of topping samples in each topping module, set timers for topping sample segments, topping samples, and/or clusters of topping samples across the topping modules, and selectively dispense and discard slices of topping samples across the topping modules as described below.

4. Hoppers and Topping Modules

Figure 2:
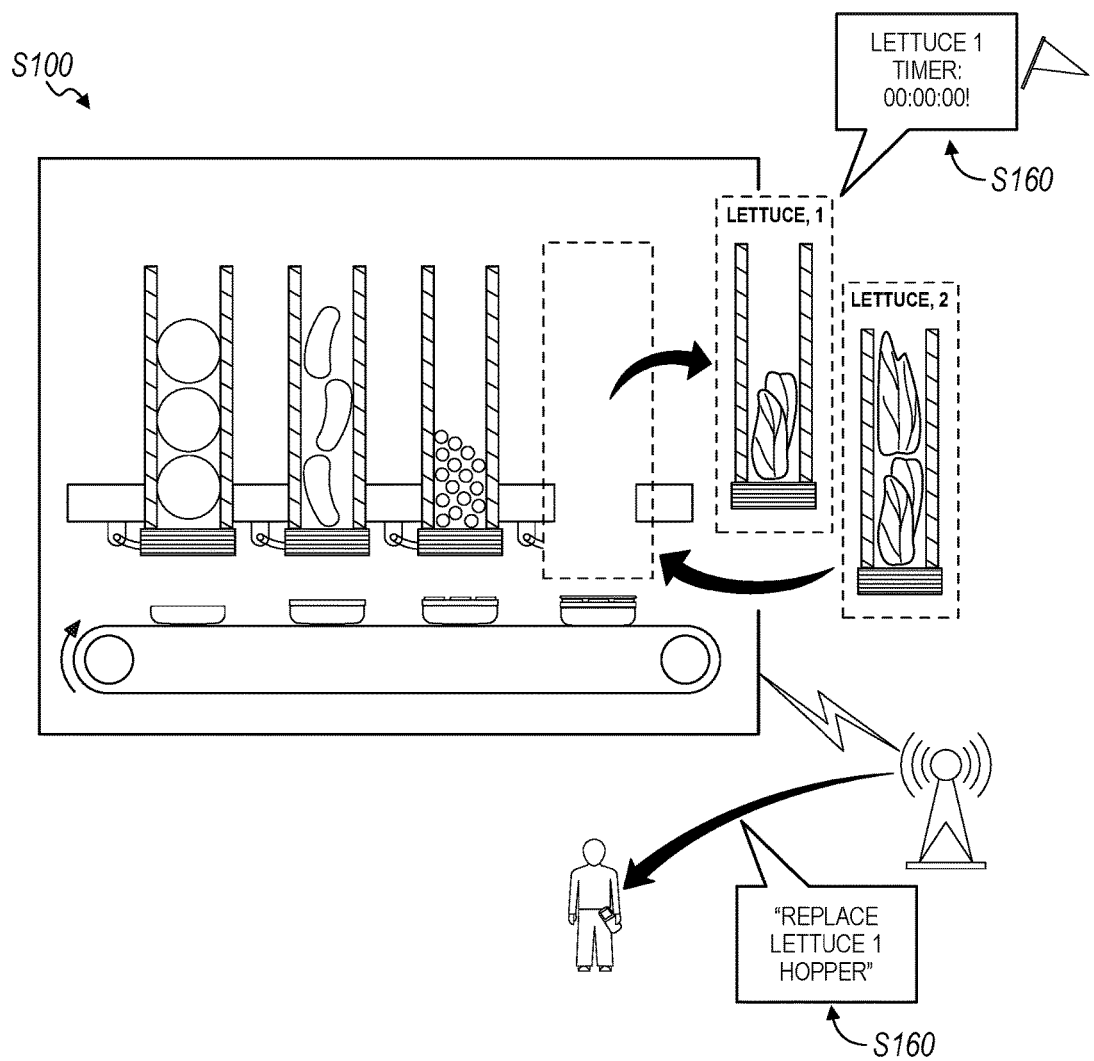
FIG. 2 is a flowchart representation of one variation of the method.

In one implementation, a topping module in the automated foodstuff assembly apparatus can include: a receptacle configured to receive a hopper; a receiver configured to receive topping samples dispensed from the hopper, a blade arranged across the receiver and configured to cut, grate, shear, or otherwise separate a section from a topping sample in the receiver; a retaining plate arranged below the blade, configured to vertically support a topping sample as the blade is driven through a topping sample, and configured to release a slice of a topping serving onto a topping vehicle (e.g., a bread bun heel) below; and an actuator system configured to selectively actuate (e.g., advance and retract) the blade and the retaining plate, such as based on topping orders assigned to topping vehicles arranged under the topping module. In this implementation, the automated foodstuff assembly apparatus can also include a conveyor arranged below the topping module and configured to sequentially advance topping vehicles into a dispense position below the topping module, to hold a topping vehicle below the topping module as a slice of a topping sample is dispensed from the topping module, and to advance the topping vehicle past the topping module, such as to a dispense position below a second, succeeding topping module, as shown in FIG. 2.

Block S110 of the method recites, at a topping module, receiving a column of topping samples including a first topping sample and a second topping sample of a first topping type, the second topping sample preceding the first topping sample in the column of topping samples. Generally, in Block S110, the topping module receives a column (or row, stack, multiple columns) of topping samples of a corresponding topping type. For example, a hopper can be prepared by an operator who collects tomatoes from a cooled compartment, manually cuts the tops and bottoms off of the tomatoes (i.e., to square the tops and bottoms of the tomatoes), inverts the hopper with closed end down, and stacks the tomatoes with flat ends abutting in the inverted hopper. In this example, the operator can then manually load the hopper—closed end up—into the topping module. Once the hopper is thus loaded into the topping module, the automated foodstuff assembly apparatus can begin tracking temperatures of topping samples within the hopper, as in Block S120, and dispensing slices of these topping samples onto topping vehicles below, as in Block S140.

In one implementation, the topping module further includes a magazine configured to receive multiple hoppers. For example, the magazine can: receive and support a row of hoppers, including a first hopper initially arranged in a discharge position over the receiver; maintain the first hopper in the discharge position as topping samples are dispensed from the first hopper into the receiver; and then index the first hopper from the discharge position into a discard position, such as when the first hopper is empty or when all or a portion of the contents of the first hopper have exceeded a heat exposure limit (e.g., exposed to a temperature greater than 41° F. more than four hours earlier after being cut by an operator). In this example, the magazine can (simultaneously) advance a second hopper from a secondary position behind the discharge position into the discharge position to enable the second hopper to dispense topping samples into the receiver. In this implementation, the topping module can receive multiple hoppers loaded with topping samples in Block S110. In this implementation, the topping module can also include thermal insulation or any other thermal barrier that thermally isolates the adjacent hoppers. The topping module can additionally or alternatively include a refrigeration unit configured to actively cool and maintain the temperature of topping samples in one or more hoppers. For example, the topping module can include one refrigeration subsystem per hopper or a first refrigeration subsystem configured to cool a hopper in the discharge position and a second refrigeration unit configured to cool hoppers behind the discharge position.

5. Temperature Sensor Integration

The topping module can include one or more temperature sensors thermally coupled to or defining a sensible field of view including a hopper and/or contents of the hopper, and the automated foodstuff assembly apparatus can sample the temperature sensor(s) throughout operation of the topping module to determine the temperature of a segment of a topping sample, the temperature of a whole topping sample, or a temperature of all or a portion of the column of topping samples in Block S120.

In one implementation, the topping module includes a statically-mounted contact-based temperature sensor (e.g., a thermocouple, a silicon bandgap temperature sensor) configured to contact a hopper installed in the topping module. In this implementation, the temperature sensor can be installed over the discharge position within the topping module and can be configured to contact the base of the hopper when installed in the discharge position over the receiver. In this implementation, the topping module can also include one or more additional statically-mounted contact-based temperature sensors arranged over the receiver and similarly configured to contact the hopper when installed in the discharge position over the receiver. In Block S120, the automated foodstuff assembly apparatus can thus sample multiple temperature sensors arranged over the receiver to collect temperature readings along the height of the hopper (and therefore along the height of the column of topping samples stored within the hopper).

In a similar implementation, the topping module includes a statically-mounted multi-dimensional temperature sensor configured to capture temperature data across all or a portion of the height of the hopper. For example, the topping module can include a thermographic camera offset from the hopper and defining a field of view including the hopper, and the automated foodstuff assembly apparatus can implement infrared thermography techniques to transform a frame output from the camera into a two-dimensional representation of temperatures across topping samples stored in the hopper, such as based on a radiation coefficient or radiation module specific to a type of topping sample designated for the hopper. In this implementation, the hopper can also be of a material substantially transparent to infrared light such that the thermographic camera can record infrared data corresponding to temperatures of topping samples within the hopper. The thermographic camera can be rigidly mounted within the topping module, and the automated foodstuff assembly apparatus can apply a static present mask to frames output by the thermographic camera in order to remove temperature data from surfaces outside of the hopper. Furthermore, the topping module can include a temperature-regulated surface outside of the hopper and within the field of view of the thermographic camera, and the automated foodstuff assembly apparatus can identify the temperature-regulated surface in a frame output by the thermographic camera and calibrate (e.g., normalize) temperatures in the frame based on a known temperature of the temperature-regulated surface. In the implementation described above in which the topping module includes a magazine configured to receive and support multiple hoppers, the thermographic camera can define a field of view that includes the discharge position and the secondary positions preceding the discharge position along the magazine; the automated foodstuff assembly apparatus can thus implement machine vision techniques and/or a multi-hopper mask to identify multiple hoppers in one frame and to extract temperature data of topping samples across the multiple hoppers from the one frame output by the thermographic camera.

In another implementation, the topping module includes a one-dimensional temperature sensor arranged on a scanning head. In this implementation, the temperature sensor and the scanning head can cooperate to scan a height of the hopper and to output a signal corresponding to temperatures along the height of the column of topping samples contained within the hopper. For example, the temperature sensor can include an infrared thermometer, and the hopper can be a material substantially transparent to infrared light, as in the foregoing implementation. In this implementation, the scanning head and temperature sensor can be offset from and aligned with the axis of the hopper, and the scanning head can pivot the temperature sensor to scan the field of view of the hopper along the centerline of the hopper. The automated foodstuff assembly apparatus can assemble temperature values output by the temperature sensor at particular scanning head positions into a line map of temperatures of topping samples within the hopper. In the implementation in which the topping module includes a magazine supporting multiple hoppers, the scan head can also be configured to reposition the temperature sensor laterally, and the automated foodstuff assembly apparatus can manipulate the scanning head to scan multiple hoppers in series.

In another example of the foregoing implementation, the scanning head can draw the temperature sensor linearly along the hopper, such as from the outside top of the hopper to the outside bottom of the hopper. The temperature sensor can alternatively define a contact-based probe, as described above, the scanning head can insert the temperature sensor into the hopper, and the automated foodstuff assembly apparatus can record signals output by the temperature sensor at discrete positions within the hopper.

In the foregoing implementation in which the topping module includes a magazine configured to hold multiple hoppers, the topping module can include a similar arrangement of one or more statically-mounted or scanning temperature sensors at secondary hopper positions (e.g., an on-deck position, an in-the-hole position) behind the discharge position. In Block S110, the automated foodstuff assembly apparatus can also sample these temperature sensors in order to separately track temperatures of topping samples stored in secondary hoppers. In this implementation, the temperature sensors can be mounted outside of the magazine such that the field of view of each temperature sensor remains constant despite the position of the magazine. Alternatively, the temperature sensors can be mounted to the magazine over their corresponding discharge and secondary positions such that a hopper loaded into the magazine is sensed by the same temperature sensor(s) as the magazine indexes the hopper into and through the discharge position. For example, for the topping module including a magazine defining multiple receivers, each receiver configured to receive a hopper as described above, the topping module can include a temperature sensor arranged in each hopper receiver, and the automated foodstuff assembly apparatus can sample temperature sensors in each receiver in which a hopper is installed until the hopper is moved into a discard position past the discharge position.

Alternatively, the automated foodstuff assembly apparatus can include one or more temperature sensors integrated into (e.g., fixed to) the hopper, and the hopper can broadcast the outputs of the integrated temperature sensor(s) to a processor within the automated foodstuff assembly apparatus over a wired or wireless connection. For example, the hopper can include a temperature sensor coupled to and powered via a radio-frequency identification (RFID) transceiver; to read a temperature from the integrated temperature sensor, the automated foodstuff assembly apparatus can thus broadcast a drive signal (e.g., in the form of radio frequency energy sufficient to power the RFID transceiver). In this example, an antenna within the RFID transceiver can harvest energy from the broadcast signal to power-up the RFID transceiver, the RFID transceiver can sample the temperature sensor, and the RFID transceiver can broadcast a value received from the temperature sensor back to the automated foodstuff assembly apparatus. In another example, the hopper can include a rechargeable battery that powers the integrated temperature regulator and an integrated wireless communication module that intermittently samples the integrated temperature sensor and broadcasts temperature data back to the automated foodstuff assembly apparatus, such as over short-range wireless communication protocol.

In the foregoing implementation, the hopper can alternatively include a wired communication jack electrically coupled to one or more temperature sensors integrated into the hopper and configured to engage a wired communication receptacle in the receiver, and the automated foodstuff assembly apparatus can sample the temperature sensor(s) over the jack-receptacle interface while the hopper is installed in the topping module.

Furthermore, in the implementation in which the hopper includes one or more integrated temperature sensors, the hopper can also include: a timer module that tracks a duration of time since the hopper is loaded with topping samples; a memory module that stores temperature values (and corresponding timestamps) output from the integrated temperature sensor(s) over time; and a (wired or wireless) communication module that transmits time series temperature values stored on the hopper to the automated foodstuff assembly apparatus. For example, before loading an empty hopper with topping samples, an operator can activate the hopper, such as by manipulating a button or switch to turn the hopper ON. Once powered ON, the hopper can sample one or more integrated temperature sensors and stored outputs of these temperature sensors in local memory; and the operator can cut tops and bottoms off of topping samples and load these topping samples into the hopper. The operator can immediately install the hopper into the receptacle in the topping module or set the hopper aside for later use, such as in a refrigerator, and the hopper can continue to record temperatures of topping samples stored in the hopper until the hopper is loaded into the topping module. Upon installation of the hopper into the receptacle, the automated foodstuff assembly apparatus can download from the hopper historic temperature data for the topping samples currently stored in the hopper and then analyze these time-based temperature data, as described below, to retroactively set and assign timers to one or more topping sample segments, topping samples, clusters of topping samples, or to the entire column of topping samples. In this example, the automated foodstuff assembly apparatus can continue to download temperature data from the temperature sensor(s) integrated into the hopper while the hopper is installed in the topping module. Alternatively, the automated foodstuff assembly apparatus can collect temperature data from external temperature sensors integrated into the topping module, as described above. The automated foodstuff assembly apparatus can thus interface with the hopper to collect, store, and access topping sample temperature data over a period of time from which topping samples are loaded into the hopper to installation of the hopper into the topping module.

6. Topping Sample Temperature

Block S120 of the method recites, at a first time, determining a first temperature of the first topping sample. (Block S120 can similarly recite, at a first time, determining temperatures along column of topping sample.) Generally, in Block S120, the automated foodstuff assembly apparatus collects temperature values of contents of the hopper to determine the temperature of one or more topping sample segments (e.g., uncut slices), topping samples, topping sample clusters, or columns of topping samples remaining in the hopper. In particular, in Block S120, the automated foodstuff assembly apparatus can collect and manipulate readings from one or more temperature sensors—thermally coupled to or within sensing range of the hopper—to interpolate, estimate, model, or otherwise determine a temperature of a segment of a topping sample, a whole topping sample (i.e., a topping sample less its top and bottom), or multiple topping samples within the hopper at a particular time. The automated foodstuff assembly apparatus can then repeat this process at a second time to interpolate, estimate, model, or otherwise determine a temperature of the segment of the topping sample, the whole topping sample, or the set of topping samples at the second time. For example, the automated foodstuff assembly apparatus can sample the temperature sensor(s) and determine the temperature of one or more topping sample segments, one or more whole topping samples, the column of topping samples, or one or more points along the column of topping samples executing Block S120 at a rate of 20 Hz, once per minute, or at any other rate during operation.

6.1 Single Temperature

In one implementation, the automated foodstuff assembly apparatus samples a single temperature sensor thermally coupled to or otherwise within sensing range of the hopper at a particular time and, based on an assumption of uniform temperature within the hopper, records the temperature output by the temperature sensor as the temperature of each topping sample in the hopper at the particular time. In this implementation, the temperature sensor can be thermally coupled to or arranged relative to the hopper in order to sense a highest temperature within the hopper. For example, for the topping module that actively cools the hopper and/or that is thermally isolated from other heating subsystems within the automated foodstuff assembly apparatus (e.g., a broiler, a cheese melting system adjacent the topping module), the temperature sensor can be positioned proximal a top of the hopper to detect highest temperatures within the hopper. In another example, the automated foodstuff assembly apparatus can include a patty grilling station adjacent the topping module, and the temperature sensor can be arranged between the patty grilling station and the hopper and directed toward the hopper to read temperatures of surfaces on or within the hopper most exposed to heat from the patty grilling station. The automated foodstuff assembly apparatus can thus sample this single temperature sensor over time and store a temperature reading output by the temperature sensor at a particular time as a temperature of all topping samples within the hopper or as a maximum possible temperature of all topping samples within the hopper at the particular time.

6.2 Interpolation

In another implementation, the automated foodstuff assembly apparatus interpolates temperatures of topping sample segments or whole topping samples within the hopper based on temperature outputs from multiple temperature sensors within the topping module. For example, within a sampling period, the automated foodstuff assembly apparatus can: record an output from a first temperature sensor thermally coupled to or otherwise within sensing range of a bottom (i.e., a dispense end) of the hopper; record an output from a second temperature sensor thermally coupled to or otherwise within sensing range of a top (e.g., a closed end) of the hopper; and then interpolate temperatures along the column of topping samples based on temperatures read from the first and second temperature sensors, known positions or fields of view of the first and second temperature sensors, and a linear interpolation model (e.g., an assumption of linear variation in temperature along the height of the hopper). The automated foodstuff assembly apparatus can then determine positions of topping samples in the column of topping samples during the sampling period, as in Block S150 described below, and map interpolated temperatures in the hopper to particular topping samples in the hopper, such as to the vertical centers of uncut slices of topping samples or to the vertical centers of whole topping samples in the hopper. For example, the automated foodstuff assembly apparatus can interpolate a temperature of each uncut slice of each topping sample in the column of topping samples during the sampling period based on the temperature read from the first temperature sensor, the temperature read from the second temperature sensor, and a slice thickness implemented by the topping module (e.g., an offset between the blade and the retaining plate in the topping module, which defines a thickness of slices cut and dispensed from the topping module).

In the foregoing implementation, the automated foodstuff assembly apparatus can sample additional temperature sensors along the height of the hopper during a sampling period and calculate a temperature versus vertical position line of best fit along the height of the hopper based on outputs of the temperature sensors and known positions of the temperature sensors. The automated foodstuff assembly apparatus can alternatively interpolate temperatures along the height of the hopper by linearly interpolating temperatures between temperatures measured at known positions along the hopper, as described above.

6.3 Scanning

In another implementation, the automated foodstuff assembly apparatus scans a temperature sensor along the height of the hoppers (or along the height of the column of temperature sensors remaining in the hopper during the scan period). In this implementation, the automated foodstuff assembly apparatus can actuate a scanning head, as described above, to reposition the temperature sensor to collect temperature data along the height of the hopper. For example, in the implementation described above in which the automated foodstuff assembly apparatus includes an infrared temperature probe, the scanning head can pivot the infrared temperature probe to read temperatures along the height of the hopper, and the automated foodstuff assembly apparatus can map a column of position-based temperature values output by the infrared temperature probe during the scan cycle to the known height of the column of topping samples during the scan cycle. In particular, the automated foodstuff assembly apparatus can map temperature data collected from the temperature probe during the scan cycle to whole topping samples or to portions (e.g., uncut slices) of topping samples stored within the hopper based on known positions of the infrared temperature probe during the scan cycle and positions of the topping samples determined in Block S150. In this example, for each segment of the hopper, the automated foodstuff assembly apparatus can: map a particular segment along the height of the hopper to a particular whole topping sample stored within the particular segment of the hopper; identify a maximum (or median) temperature recorded by the temperature probe along the particular segment of the hopper; and store the maximum temperature recorded along the particular segment in a register corresponding to the particular topping sample.

In another example, the automated foodstuff assembly apparatus can identify or estimate an approximate center of each topping sample (or an approximate center of each uncut slice in each topping sample) stored in the hopper, sequentially reposition the temperature probe to scan the approximate center of each topping sample within the hopper, and then record temperatures output by the infrared temperature probe in registers corresponding to each topping sample (or to each uncut slice in each topping sample). The automated foodstuff assembly apparatus can thus store empirical temperature data in registers or other databases for each discrete topping sample or each segment of each topping sample stored in the hopper.

However, the automated foodstuff assembly apparatus can collect temperature in any other way, implement any other method or technique to map these temperature data to one or more topping samples within the hopper, and store these temperature data in one or more registers, databases, or other data storage systems assigned to corresponding topping samples, portions of topping samples, or positions along the height of the hopper.

7. Temperature Thresholds and Timers

Figure 3:
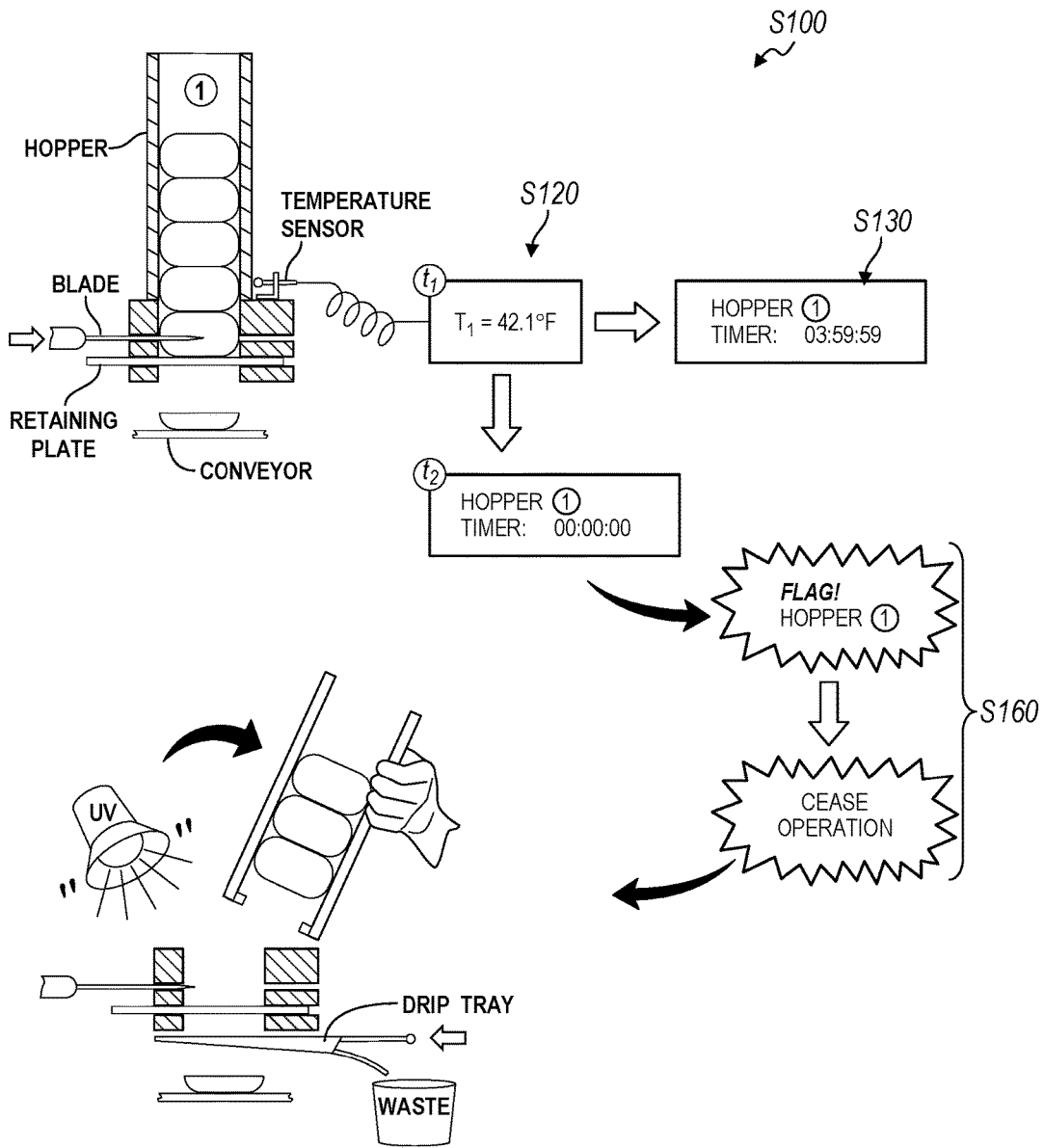
FIG. 3 is a flowchart representation of one variation of the method.

Block S130 of the method recites, in response to the first temperature of the first topping sample exceeding a threshold temperature, setting a first timer assigned to the first topping sample. (Block S130 can similarly recite, in response to the particular temperature at a particular position along the column of topping samples exceeding a threshold temperature, setting a timer assigned to the particular position along the column of topping samples.) Generally, in Block S130, the automated foodstuff assembly apparatus can: assign a timer to the hopper (e.g., to the full column of topping samples contained within the hopper), as shown in FIGS. 2 and 3; to a subset of topping samples stored in the hopper; to a particular topping sample stored within the hopper, as shown in FIG. 1; or to a particular portion (e.g., an uncut slice) of a particular topping sample stored within the hopper. In Block S130, the automated foodstuff assembly apparatus can then set the timer for a threshold duration of time in response to a determined temperature of contents within the hopper, of a topping sample, or of a portion of a topping sample exceeding a threshold temperature, such as specified in a food handling regulation.

In one example, in response to determining that a first topping sample stored in the hopper has reached a temperature in excess of a threshold temperature of 41° Fahrenheit (5° Celsius, such as specified in a food handling regulation) in Block S120, the automated foodstuff assembly apparatus assigns a first timer to the first topping sample and sets the first timer for a duration of four hours. Once the first timer assigned to the first topping samples is set and active, the automated foodstuff assembly apparatus can continue to monitor the position and temperature of the first sample. In particular, the automated foodstuff assembly apparatus can permit the topping module to cut a slice from the first topping sample and to dispense the slice onto a topping vehicle as long the first timer has not expired prior to the slice being cut from the first topping sample. However, if a temperature of the first topping sample is determined to exceed a high threshold temperature of 70° F. before first timer expires, upon expiration of the first timer, the automated foodstuff assembly apparatus can flag for disposal any portion of the first topping sample remaining in the hopper. In this example, if the automated foodstuff assembly apparatus determines that the temperature of the first topping sample has not exceeded the high threshold temperature of 70° F. upon expiration of the first timer and all or a portion of first topping sample remains in the hopper, the automated foodstuff assembly apparatus can assign a second timer to the first topping sample and set the second timer for a duration of two hours, thereby extending a period of time in which slices from the first topping sample can be served. Furthermore, once the second timer expires or if a temperature of the topping sample is determined to have exceeded the high threshold temperature of 70° F. before the second timer expires, the automated foodstuff assembly apparatus can immediately flag for disposal any portion of the first topping sample remaining in the hopper.

Therefore, as in the foregoing example, the automated foodstuff assembly apparatus can set and assign one or more timers to a particular topping sample (or to a particular section of a topping sample, to a particular cluster of topping samples, etc.) over time based on determined temperatures of the particular topping sample in order to comply with defined food handling regulations. In particular, the automated foodstuff assembly apparatus can implement, selectively set, and assign timers to topping samples based on temperatures and time limits for serving foodstuffs defined in food handling regulations. The automated foodstuff assembly apparatus can also apply buffers to timer durations and/or temperature triggers. For example, for a food handling regulation that specifies a maximum duration of six hours between exposure of a foodstuff to a temperature over 41° F., the automated foodstuff assembly apparatus can define a trigger temperature of 39° F. for a four-hour timer.

Furthermore, when setting a timer for a hopper, a topping sample, or a portion of a topping sample, etc., the automated foodstuff assembly apparatus can anticipate and/or compensate for a known or projected period between dispensation of a slice from a topping sample and consumption by a patron. For example, the automated foodstuff assembly apparatus can set a first timer for a duration specified in a food handling regulation less a maximum anticipated duration of time between when a slice of a topping sample dispensed from the topping module will be collected and consumed by a patron (e.g., eight minutes for food orders fulfilled by the automated foodstuff assembly apparatus arranged within a restaurant or other retail space). The automated foodstuff assembly apparatus can also dynamically set the duration of a timer, such as based on whether all or a subset of food orders in a queue assigned to the automated foodstuff assembly apparatus are designated for "eat-in" (e.g., corresponding to an eight-minute dispensation to consumption time and a 3:52 timer duration) or designed for "carry-out" (e.g., corresponding to an 32-minute dispensation to consumption time and a 3:28 timer duration). Similarly, in response to a temperature of the first topping sample exceeding the temperature threshold (e.g., 41° F.), the automated foodstuff assembly apparatus can set and assign both an "eat-in" timer and a "carry-out" timer to the first topping sample and then selectively discard a slice cut from the first topping sample or dispense the slice onto a topping vehicle based on whether a food order corresponding to the topping vehicle designates eat-in or carry-out and the status of the corresponding timer.

The automated foodstuff assembly apparatus can also set and assign one timer per segment (e.g., uncut slice) of a topping sample. For example, in Block S120, the automated foodstuff assembly apparatus can: set and assign a first timer assigned to a first uncut slice of the first topping sample in response to a determined temperature of the first uncut slice exceeding the threshold temperature; and set and assign a second timer to a second uncut slice of the first topping sample in response to a determined temperature of the second uncut slice exceeding the threshold temperature. In the foregoing example, the automated foodstuff assembly apparatus can set and assign the first and second timers to corresponding segments of the first topping sample based on temperature data collected during a single sampling period; alternatively, the automated foodstuff assembly apparatus can set and assign the first timer based on temperature data collected during a first sampling period and can set and assign the second timer based on temperature data collected during a second sampling period preceding or succeeding the first sampling period. In the foregoing example, the second uncut slice of the topping sample can be interposed between an output end of the hopper and the first uncut slice in the topping sample, and the topping module can dispense the second uncut slice of the topping sample onto a topping vehicle prior to expiration of the second timer and later flag the first uncut slice—in the same topping samples—for disposal if the first uncut slice remains in the hopper when the first timer expires.

The automated foodstuff assembly apparatus can implement similar methods and techniques to set and assign timers to various topping samples (or clusters of adjacent topping samples) within the hopper. For example, the automated foodstuff assembly apparatus can: during a first sampling period, determine a first temperature of the first topping samples based on temperature data collected during a first sampling period; set a first timer assigned to the first topping sample if the first temperature exceeds the threshold temperature; determine a second temperature of the second topping sample based on temperature data collected during a second sampling period succeeding the first sampling period; and set a second timer assigned to the second topping sample if the second temperature exceeds the threshold temperature. In this example, for the second topping sample interposed between the output end of the hopper and the first topping sample, the automated foodstuff assembly apparatus can selectively discard the second topping sample or dispense slices from the second topping sample onto topping vehicles below based on the state of the second timer and independently of the state of the first timer.

However, the automated foodstuff assembly apparatus can implement any other method or technique to assign one or more timers—of any other suitable duration—to a particular section of a topping sample, to a whole topping sample, to a cluster of topping samples, and/or to a column of topping samples stored in the hopper.

8. Dispensing Topping Slice

Figure 7:
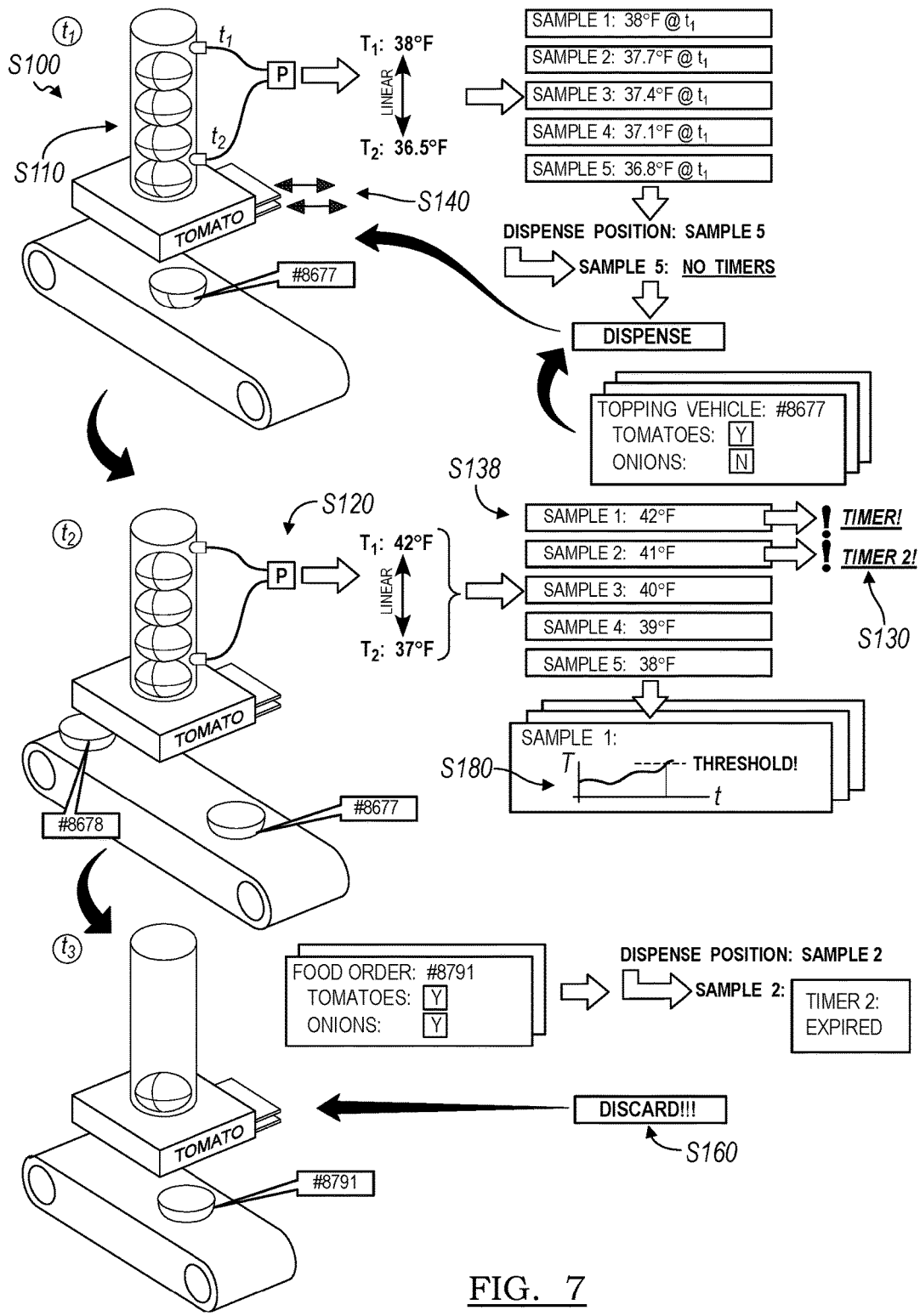
FIG. 7 is a flowchart representation of one variation of the method.

Block S140 of the method recites cutting a slice from the second topping sample. Generally, in Block S140, the automated foodstuff assembly apparatus selectively dispenses a slice of a topping sample from the topping module onto a topping vehicle, such as based on a request for the topping type in a food order corresponding to the topping vehicle, as shown in FIGS. 1, 3, and 7. In one implementation, to cut and dispense a slice of a topping sample from the topping module, the automated foodstuff assembly apparatus can: retract the blade in the topping module to drop an adjacent topping sample onto the retaining plate; advance the blade to sever a slice from the topping sample; retract the retaining plate to release the slice from the topping module; and advance the retaining plate to reset the topping module. Alternatively, the topping module can include a retaining plate longitudinally offset ahead of and coupled to the blade, and the topping module can advance the blade and retaining plate assembly to cut and release a slice of the topping sample from the topping module and then retract the blade and retaining plate assembly to reset the topping module.

In one example, when a topping vehicle associated with a food order specifying a topping type dispensed from the topping module is advanced into a dispense position below the topping module, the automated foodstuff assembly apparatus can verify a particular topping sample currently arranged over the blade. In particular, if no timer has been set for the particular topping sample or if a timer assigned to the particular topping sample has not yet expired, the automated foodstuff assembly apparatus can clear the topping sample for consumption and trigger the topping module to actuate the blade to cut and dispense a slice from the particular topping sample onto the topping vehicle. However, in this example, if the particular topping sample currently arranged over the blade is associated with a timer that has expired (or if the particular topping sample is associated with a timer that will expire before the completed topping vehicle is served to a patron), the automated foodstuff assembly apparatus can execute Block S160 to discard the particular topping sample, can discard other topping samples in immediate contact with the particular topping sample until a verified topping sample enters a cutting position over the blade, and/or can sanitize the blade and other surfaces within the topping module in contact with the particular topping sample in preparation to cut a slice from the verified topping sample. Therefore, in this example, the automated foodstuff assembly apparatus can selectively execute Block S160 to maintain a verified topping sample (i.e., a topping sample not associated with an expired timer) in a cutting position adjacent the blade in preparation for immediate dispensation of a slice of a topping sample through operation of the automated foodstuff assembly apparatus.

However, the automated foodstuff assembly apparatus can implement any other method or technique to verify a topping sample and to selectively cut and dispense slices of topping samples onto topping vehicles throughout operation.

9. Topping Sample Position Tracking

Block S150 of the method recites, at a second time succeeding the first time, in response to dispensation of the slice of the second topping sample from the topping module onto a topping vehicle, tracking a position of the first topping sample within the topping module. (Block S150 can similarly recite, in response to dispensation of the slice from the column of topping samples onto topping vehicles, tracking shifts in the particular position along the column of topping samples—corresponding to an active timer—toward the dispense end of the topping module.) Generally, in Block S150, the automated foodstuff assembly apparatus tracks changes in positions of topping samples (or portions of topping samples) within the hopper as slices are cut and dispensed from topping samples and as the column of topping samples shortens over time, as shown in FIG. 1.

In one implementation, the automated foodstuff assembly apparatus implements dead reckoning techniques to track positions of topping samples within the hopper. In particular, in this implementation, the automated foodstuff assembly apparatus can estimate locations of topping samples (or portions of topping samples) within the hopper based on common, average, or controlled heights of topping samples loaded into the hopper, a known thickness of slices cut from topping samples in the hopper (e.g., a static offset between the blade and the retaining plate), an initial number of topping samples loaded into the hopper, and a number of slices already cut (e.g., dispensed or discarded) from the hopper since the hopper was loaded into the topping module. When the hopper is first loaded into the topping module, the automated foodstuff assembly apparatus can determine a height of the topping sample column based on the foregoing parameters and can then segment the column of topping samples, such as by 0.25" segments (e.g., corresponding to the slice thickness of the topping module), by whole topping samples, by clusters of topping samples (e.g., three adjacent topping samples), or by discrete lengths (e.g., 2" lengths) of topping sample. The automated foodstuff assembly apparatus can also allocate timers and temperature registers for each discrete segment defined in the column of topping samples and can map these timers and temperature registers to positions of corresponding topping sample segments, such as relative to the blade or relative to the top of the hopper. Following each actuation of the blade and retaining plate in Block S140 during operation, the automated foodstuff assembly apparatus can index a slice counter and then shift the position assignments for the timers and temperature registers based on the new value on the slice counter, thereby maintaining alignment between virtual timers and temperature registers and their corresponding topping samples in the hopper.

In another implementation, the automated foodstuff assembly apparatus includes a height (or distance) sensor coupled to or within sensing range of the topping samples within the hopper and outputs a signal corresponding to the height of the stack of topping samples within the hopper. For example, the topping module can include a mechanical, capacitive, acoustic, or other height sensor arranged over and offset above the blade such that the height sensor can sense a distance to a top of a topping sample in a hopper when the hopper is inserted in the discharge position over the blade. In this example, the height sensor can include an infrared or acoustic distance, can be mounted at a known distance over the blade, and can output a signal corresponding to the distance of a surface between the height sensor and the blade (e.g., a top of a topping sample in the hopper); based on the known position of the height sensor and an output of the height sensor during a particular sampling period; the automated foodstuff assembly apparatus can thus determine a height of the column of topping samples in the hopper during the sample period. In this example, the automated foodstuff assembly apparatus can sample the height sensor after the hopper is loaded into the discharge position and before a first slice of the topping is dispensed from the hopper in order to determine an initial height of the column of topping samples and to assign initial positions to timers and registers for the hopper. The automated foodstuff assembly apparatus can continue to sample the height sensor, such as at regular intervals (e.g., a 1 Hz) or after each blade actuation cycle, in order to track the height of the column of toppings samples in the hopper and to update the assigned positions of the timers and registers for the hopper in Block S150. In this implementation, the height sensor can alternatively be integrated into the hopper, and the hopper can communicate signals output from the height sensor to the automated foodstuff assembly apparatus, such as over wired or wireless communication protocol, as described above.

In another implementation, the automated foodstuff assembly apparatus further incorporates an optical sensor (e.g., an RGB camera) defining a field of view including the hopper, and the automated foodstuff assembly apparatus implements machine vision techniques: to identify topping samples stored in the hopper from a digital image captured with the optical sensor; to identify the hopper in the digital image; and to determine relative positions of the topping samples within the hopper. The automated foodstuff assembly apparatus can then map the temperature registers and timers to select positions along the hopper based on determined positions of the topping samples within the hopper. In this implementation, the automated foodstuff assembly apparatus can also implement machine vision and object tracking techniques to track the position of each topping sample in the hopper across a sequence of digital images recorded by the optical sensor, and the automated foodstuff assembly apparatus can update position assignments for the temperature registers and timers accordingly. In this implementation, the optical sensor can define a field of view including multiple hoppers arranged within one topping module and/or across multiple topping modules, and the automated foodstuff assembly apparatus can implement machine vision techniques to identify the multiple hoppers and topping samples contained therein from a single image recorded by the optical sensor.

However, the automated foodstuff assembly apparatus can implement any other method or techniques to track positions of topping samples within the hopper over time. Based on the determined position of a particular topping sample segment, whole topping sample, or topping sample cluster in the hopper at each subsequent sampling period, the automated foodstuff assembly apparatus can shift a position associated with the virtual (running or static) timer and temperature register assigned to the particular topping sample segment, whole topping sample, or topping sample cluster. For each subsequent sampling period, the automated foodstuff assembly apparatus can insert temperature data collected during the sampling period into corresponding registers in order to maintain temperature records for each topping sample segment, whole topping sample, or topping sample cluster in the hopper during operation. The automated foodstuff assembly apparatus can similarly update positions associated with timers assigned to topping sample segments, whole topping samples, or topping sample clusters as the topping module dispenses slices of topping samples from the hopper. However, the automated foodstuff assembly apparatus can implement any other method or technique to track topping samples within the hopper over time and to maintain a virtual representation of temperatures and timers for the topping samples over time in Block S150.

Furthermore, in Block S150, the automated foodstuff assembly apparatus can transform determined positions of topping samples within the hopper into target measurement positions for one or more manipulatable temperature sensors within the topping module, such as to set a scan distance or to specify discrete probe positions along the hopper for a scanning-type infrared temperature probe, as described above.

10. Discarding Exposed Samples

Block S160 of the method recites, in response to expiration of the first timer prior to dispensation of a final portion of the first topping sample from the topping module, disqualifying the final portion of the first topping sample from dispensation onto a topping vehicle. (Block S160 can similarly recite, in response to expiration of the first timer prior to dispensation of a particular topping sample, coinciding with the particular position along the column of topping samples, from the topping module, disqualifying the particular topping sample from dispensation onto a topping vehicle.) Generally, the automated foodstuff assembly apparatus executes Block S160 to designate a topping sample (or a segment of a topping sample, a remaining portion of a topping sample, a cluster of topping samples, or all topping samples, etc.) currently stored in a hopper for disposal when a temperature-based time control window for the topping sample has been exceeded. In particular, the automated foodstuff assembly apparatus can flag a topping sample for disposal (i.e., not for dispensation onto a topping vehicle or for service to a customer) in response to expiration of a timer assigned to the topping vehicle.

As described above, the automated foodstuff assembly apparatus can set a timer (e.g., of a duration of four hours) for the entire contents of the hopper if a determined temperature in at least one region of the hopper exceeds a low threshold temperature (e.g., 41° F.). If any topping samples or segments of a topping sample remain in the hopper when the timer expires, the automated foodstuff assembly apparatus can cease dispensation of any topping sample from the hopper and flag the hopper for removal from the topping module in Block S160.

The automated foodstuff assembly apparatus can set a timer for a cluster of (e.g., three adjacent) topping samples stored in the hopper if a determined temperature in at least one portion of the topping sample cluster exceeds the low threshold temperature. If any topping sample or segments of a topping sample in the cluster remain in the hopper when the timer expires, the automated foodstuff assembly apparatus can cease dispensation of any topping sample from the hopper, flag the hopper for removal from the topping module, and/or automatically dispose of the topping sample clusters from the hopper and continue dispensing slices of other topping samples not associated with expired timers in Block S160.

Similarly, the automated foodstuff assembly apparatus can set a timer for a whole topping sample stored in the hopper if a determined temperature in at least one region of the topping sample exceeds the low threshold temperature. If any portion of the topping sample remains in the hopper when the timer expires, the automated foodstuff assembly apparatus can cease dispensation of any topping sample from the hopper, flag the hopper for removal from the topping module, and/or automatically dispose of the topping sample from the hopper and continue dispensing slices of other topping samples not associated with expired timers in Block S160. The automated foodstuff assembly apparatus can implement similar methods and techniques to set and handle a timer specific to a segment (e.g., an uncut slice) of a topping sample.

10.1 Dispense Expired Contents

In one implementation, the automated foodstuff assembly apparatus automatically disposes of "expired" topping samples (i.e., topping samples associated with an expired timer(s)), such as into a waste container arranged within the topping module and marked "contaminated food" or "food waste." In one example, when a topping sample expires and then reaches the blade, the automated foodstuff assembly apparatus can advance a disposal chute into position under the outlet of the topping module and then trigger the topping module to cut a slice from the topping sample; the disposal chute can thus catch and guide the slice of the topping sample into the waste container below. In this example, the automated foodstuff assembly apparatus can repeatedly trigger the topping module to cut slices from the expired topping sample until a final portion of the expired topping sample is dispensed from the topping module and discarded into the waste container. In a similar example, when a topping sample expires and then reaches the blade, the automated foodstuff assembly apparatus can move the topping module into position over the waste container and then actuate the blade and retaining plate to cut and dispense slices of the expired topping sample directly into the waste container.

In a yet another example, when a timer associated with a topping sample at any position within the hopper expires, the automated foodstuff assembly apparatus advances a disposal chute under the topping module and triggers the blade repeatedly to cut and dispense the entire contents of the topping module into the waste container. In a similar example the topping module can define a static disposal chute succeeding the receiver, defining a diameter approximating the internal diameter of the hopper, and terminating in a waste container. In this example, when a timer associated with a topping sample at any position within the hopper expires, the automated foodstuff assembly apparatus can advance the hopper forward from the discharge position into a discard position over the chute, thereby releasing the entire contents of the hopper down the chute and into the waste container, as shown in FIG. 1.

10.2 Automatic Hopper Replacement

Figure 6:
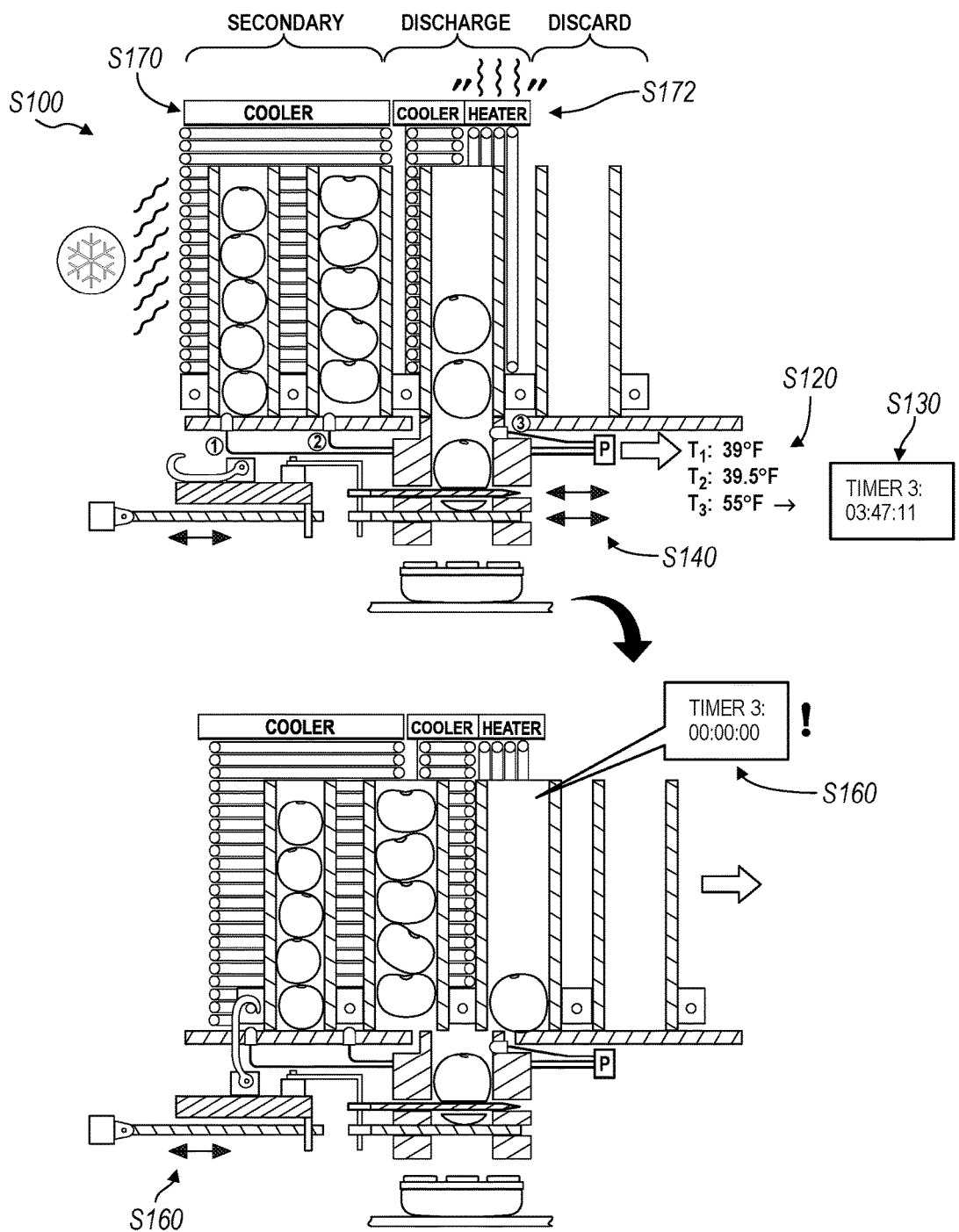
FIG. 6 is a flowchart representation of one variation of the method.

In another implementation, when a timer associated with a topping sample at any position within the hopper expires, the automated foodstuff assembly apparatus triggers the magazine in the topping module to index the hopper forward from the discharge position into a discard position and to index a second hopper (containing topping samples not associated with expired timers) into the discharge position, as shown in FIG. 6. The topping module can then implement the foregoing methods and techniques to track temperatures of topping samples in the second hopper and to selectively dispense and discard topping samples in the second hopper.

Similarly, the automated foodstuff assembly apparatus can trigger the magazine to index the hopper from the discharge position into the discard position and then issue a prompt or notification (e.g., an audible or visual notification at the automated foodstuff assembly apparatus, a textual notification transmitted to a remote display) to manually install a second hopper containing a fresh column of topping samples into the topping module.

10.3 Topping Module Immobilization

In another implementation, when a timer associated with a topping sample at any position within the hopper expires, the automated foodstuff assembly apparatus ceases operation of the topping module and blocks further dispensation of slices from the hopper. In this implementation, the automated foodstuff assembly apparatus can also extend a drip tray under the topping module to catch fluids discharged from the topping samples and to prevent fluids discharged from the topping samples from reaching a conveyor or topping vehicles below, as shown in FIG. 3. The automated foodstuff assembly apparatus can also issue a flag for manual removal of the hopper from the topping module, such as by issuing an audible or visual alarm at the automated foodstuff assembly apparatus and/or by transmitting a notification to a local display (e.g., a tablet computer accessed by an operator, a display arranged in a food preparation area of a restaurant) to exchange the hopper, as shown in FIG. 2.

However, the automated foodstuff assembly apparatus can handle expiration of a timer corresponding to a topping sample segment, a whole topping sample, a cluster of topping samples, or a topping sample column in any other way in Block S160. Furthermore, if a timer corresponding to a topping sample is still running (i.e., not expired) when a final portion of the topping sample is dispensed from the topping module, the automated foodstuff assembly apparatus can clear and discard the timer.

11. Disinfection

The automated foodstuff assembly apparatus can further disinfect (or "substantially sterilize") a blade, the retaining plate, and/or other surfaces of the hopper or topping module in response to expiration of a timer corresponding to a topping sample currently stored within the hopper.

In one implementation, the topping module includes an ultraviolet germicidal irradiation (UVGI) device, such as a mercury-vapor lamp arranged over the blade and/or along the hopper. In this implementation, when a timer associated with a topping sample at any position within the hopper expires, the automated foodstuff assembly apparatus can pause operation of the topping module and activate the mercury-vapor lamp for a predetermined period of time of thirty seconds before resuming operation of the topping module, as shown in FIG. 3. During a disinfection cycle, the topping module can also selectively advance and retract the retaining plate and the blade to expose surfaces on the receiver, on the blade, on the retaining plate, and below the retaining plate, etc. to ultraviolet light. In this implementation, the topping module can also include a series of blinds arranged about the hopper, and the automated foodstuff assembly apparatus can close the blinds when the mercury-vapor lamp is activated to shield patrons and other areas of the automated foodstuff assembly apparatus from UV light.

The topping module can also include: a wiper system configured to wipe food waste (e.g., fluid, seeds, torn endocarp) from the blade and retaining plate; and a disposal tray or container configured to receive waste caught by the wiper system. In response to expiration of a topping sample in the hopper, the automated foodstuff assembly apparatus can additionally or alternatively: pause operation of the topping module; trigger the wiper system to wipe food material off of the blade and the retaining plate and into the waste tray; and activate the mercury-vapor lamp for a predetermined period of time before resuming operation of the topping module. In this implementation, the automated foodstuff assembly apparatus can further include a spray system configured to spray a food-safe disinfectant onto surfaces with the topping module, such as predominately the blade and the retaining plate; the automated foodstuff assembly apparatus can activate the spray system to chemically disinfect the topping module, such as once the wiper system has wiped food waste from the blade and retaining plate into the waste tray. For example, in this implementation, the wiper system can include a set of wipers fixed in the receiver and configured to wipe fluid and other food waste from the blade and the retaining plate when actuated, and the automated foodstuff assembly apparatus can actuate the wiper system by inserting the disposal tray under the receiver and actuating the blade and retaining plate through an extended advance and extended retract cycle to wipe food waste off of the blade and retaining plate and to release this food waste into the disposal tray.

In another implementation, the topping module includes a heating element coupled to the blade and to the retaining plate. In response to expiration of a topping sample in contact with the blade, the automated foodstuff assembly can activate the heating element to heat the blade and retaining plate to a target disinfecting temperature for a target period of time, thereby disinfecting the blade and the retaining plate. In still another implementation, in response to expiration of a topping sample stored in the hopper, the automated foodstuff assembly apparatus can charge the receiver and the hopper with steam over a predetermined duration of time in order to disinfect the receiver and the hopper.

However, the automated foodstuff assembly apparatus can implement any other one or more methods or techniques to disinfect surfaces within the topping module. Furthermore, the automated foodstuff assembly apparatus can disinfect surfaces within the topping module while the hopper is in situ in the discharge position over the blade, such as once an expired topping sample or expired topping sample segment has been discharged from the hopper into a waste container. The automated foodstuff assembly apparatus can additionally or alternatively disinfect surfaces within the topping module once a hopper containing an expired topping sample has been advanced ahead of the discharge position over the blade, such as to a discard position. The automated foodstuff assembly apparatus can also disinfect surfaces within the topping module once a second hopper has been advanced into the discharge position following expiration of a topping sample with the preceding hopper. However, the automated foodstuff assembly apparatus can automatically implement disinfecting techniques in any other order and at any other time before, during, and/or after an operating period.

12. Re-Queuing

In one configuration, the (first) automated foodstuff assembly apparatus operates in conjunction with a second automated foodstuff assembly apparatus within a restaurant, a retail space, etc. In this configuration, a computer system (e.g., a local food ordering system or a remote server receiving food orders entered through a native ordering application executing on patrons' smartphones) can: receive food orders from patrons over time; and insert food orders received from patrons into a first queue assigned to the first food assembly apparatus and into a second queue assigned to the second food assembly apparatus. The first and second automated foodstuff assembly apparatuses can thus independently assemble hamburgers according to food orders inserted into their corresponding queues.

Figure 4:
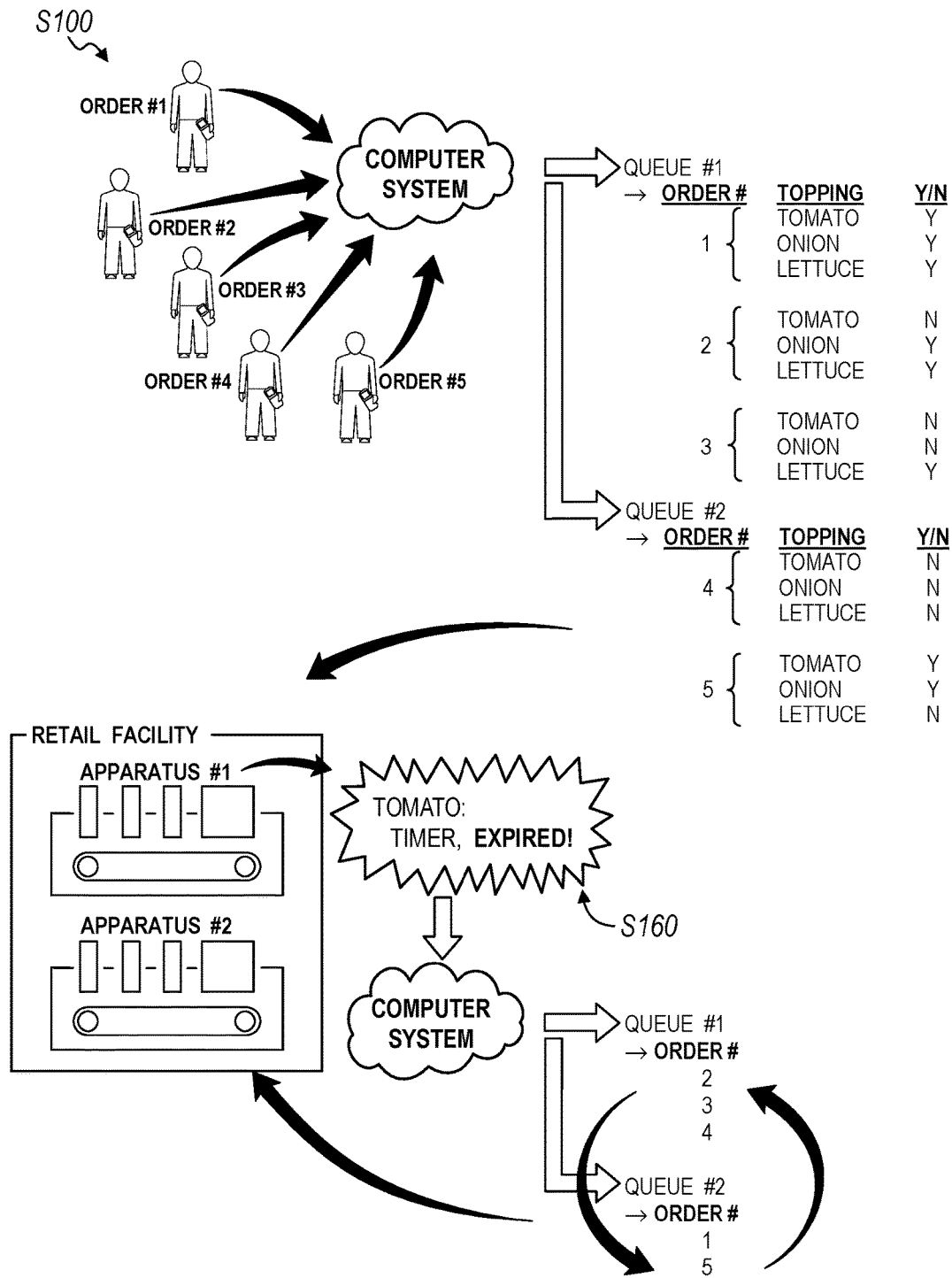
FIG. 4 is a flowchart representation of one variation of the method.

In this configuration, when a topping sample of a first topping type in a first topping module in the first automated foodstuff assembly apparatus expires such that the first topping type is not available for serving from the first automated foodstuff assembly apparatus, the computer system can redistribute food orders across the first and second automated foodstuff assembly apparatuses substantially in real-time in order to continue fulfillment of the food orders. For example, in response to expiration of a topping sample of the first topping type in a first topping module in the first automated foodstuff assembly apparatus, the computer system can: identify a first set of food orders—in the first queue assigned to the first automated foodstuff assembly apparatus—that specify inclusion of the first topping type; remove this first set of food orders from the first queue; and insert this first set of food orders into the second queue assigned to the second automated foodstuff assembly apparatus, as shown in FIG. 4. In particular, the computer system can shift food orders specifying inclusion of the first topping type from the first automated foodstuff assembly apparatus in which the first topping module containing topping samples of the first topping type is currently disabled to the second automated foodstuff assembly apparatus in which a topping module containing topping samples of the first topping type is currently active and enabled such that these orders can continue to be processed and completed with minimal additional delay. Similarly, in this example, the computer system can: identify a second set of food orders—in the second queue assigned to the second automated foodstuff assembly apparatus—that do not specify inclusion of the first topping type; remove this second set of food orders from the second queue; and insert this second set of food orders into the first queue assigned to the first automated foodstuff assembly apparatus. In particular, the computer system can identify the second set of food orders—initially assigned to the second automated foodstuff assembly apparatus—that can be fulfilled by the first automated foodstuff assembly apparatus despite deactivation of the first topping module in the first automated foodstuff assembly apparatus, and the computer system can redistribute this second set of food orders to the first automated foodstuff assembly apparatus in order to make room in the second queue for the first set of food orders to achieve minimal additional delay in delivery of food orders in both the first and second queues.

The computer system can implement the foregoing methods and techniques to shift one food order from the first queue to the second queue and vice versa, to shift a predetermined number of food orders from the first queue to the second queue and vice versa, or to dynamically shift any other number of food orders from the first queue to the second queue and vice versa, such as based on an estimated time to replace the hopper and sterilize the first topping module in the first automated foodstuff assembly apparatus. However, the computer system can implement any other method or technique to redistribute food orders between two or more automated foodstuff assembly apparatuses in response to expiration of a topping sample and deactivation of a topping module.

13. Topping Module Surfaces

The automated foodstuff assembly apparatus can implement similar methods and techniques to track temperatures of surfaces within the topping module (e.g., the hopper, the blade, the retaining plate) that contact cut topping samples or fluids discharged from cut topping samples. For example, the automated foodstuff assembly apparatus can sample a temperature sensor thermally coupled to the blade in the topping module in order to track the temperature of the blade during operation. In this example, the automated foodstuff assembly apparatus can set a timer assigned to the blade if the temperature of the blade (or any portion of the blade in contact with topping samples or fluids discharged from topping samples) rises about the threshold temperature (e.g., 41° F.), as described above. Once the blade timer expires, the automated foodstuff assembly apparatus can flag the blade (or the whole topping module) for cleaning, such as by manual removal and cleaning by an operator. Alternatively, once the blade timer expires, the automated foodstuff assembly apparatus can pause operation and automatically disinfect the blade (and other surfaces within the topping module), such as described above. The automated foodstuff assembly apparatus can similarly track temperatures of the retaining plate, the hopper(s), and/or any other surface within the topping module, can set and assign timers based on temperatures of these structures, and automatically trigger manual cleaning or automatically disinfect such surfaces based on statuses of these timers.

14. Temperature Control

Figure 5:
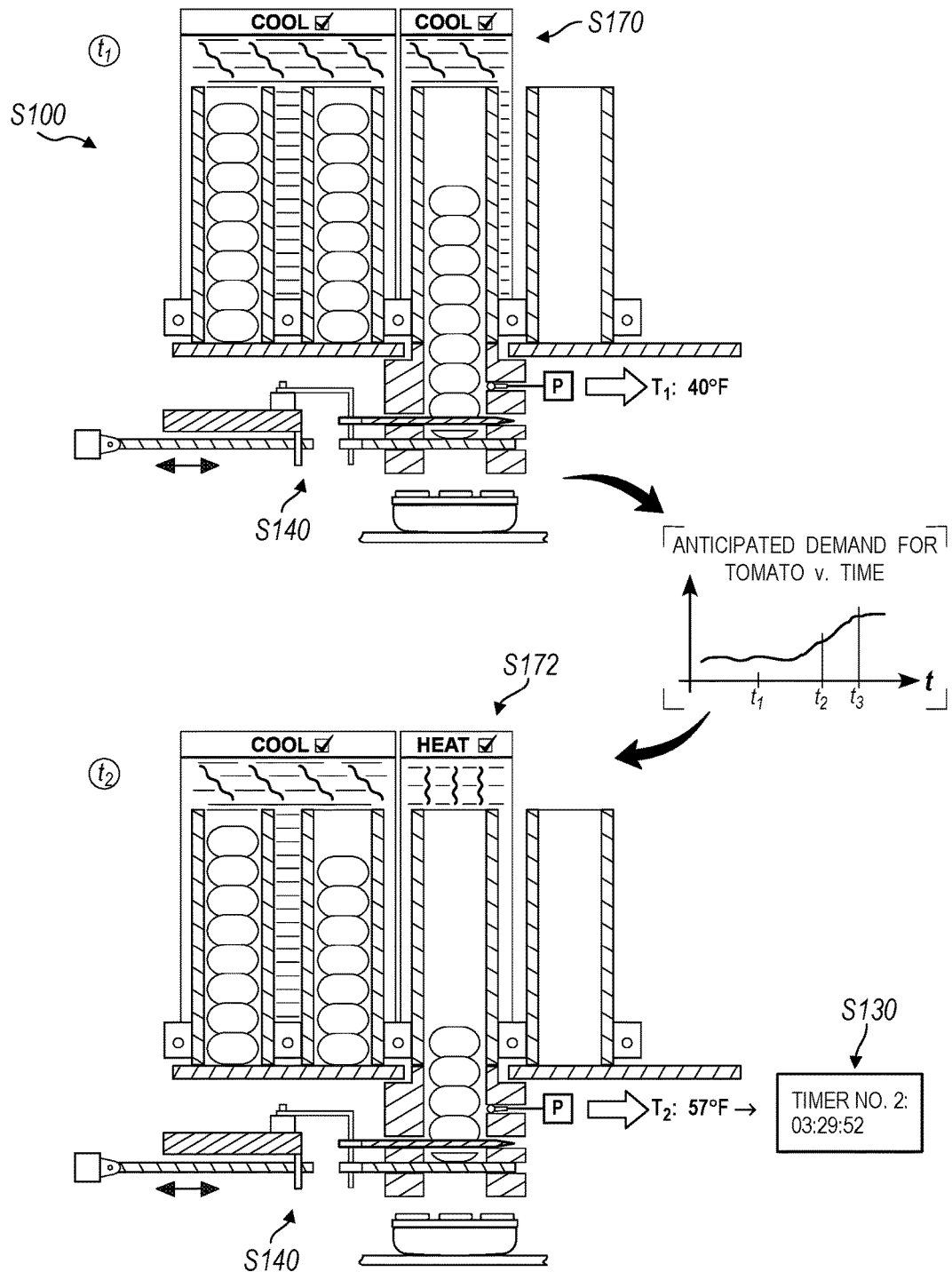
FIG. 5 is a flowchart representation of one variation of the method.

As shown in FIG. 5, one variation of the method includes: at a topping module, receiving a hopper containing a column of topping samples of a first topping type in Block S110; and, during a first period of time, maintaining the column of topping samples within a first temperature range less than a low threshold temperature in Block S170, sequentially cutting slices from the column of topping samples in Block S140, and dispensing slices from the column of topping samples onto topping vehicles in Block S140. This variation of the method also includes, during a second period of time succeeding the first period of time: maintaining a remaining portion of the column of topping samples within a target consumption temperature range greater than the low threshold temperature in Block S172; and setting a timer for the remaining portion of the column of topping samples in Block S120. Furthermore, this variation of the method includes, prior to expiration of the timer: sequentially cutting slices from the column of topping samples in Block S140; and dispensing slices from the remaining column of topping samples onto topping vehicles in Block S140. Finally, this variation of the method includes, in response to expiration of the timer prior to dispensation of a final portion of the remaining column of topping samples, disqualifying the final portion of the remaining column of topping samples from dispensation onto a topping vehicle in Block S160.

Generally, in this variation, the automated foodstuff assembly apparatus can actively control the temperature of topping samples in the hopper and can selectively raise the temperature of topping samples in the hopper in preparation for serving, as shown in FIG. 6. In particular, a topping type can be associated with a preferred consumption temperature (or preferred consumption temperature range) greater than the low temperature threshold specified in food handling requirements or in food codes for storing, handling, and serving foodstuffs; in preparation for dispensing a slice from a topping sample of the topping type stored in the topping module, the automated foodstuff assembly apparatus can raise (or maintain) a temperature of the topping sample to the preferred consumption temperature. The automated foodstuff assembly apparatus can thus expose the topping sample (and other topping samples) in the hopper to a temperature in excess of the low temperature threshold such that slices of the topping type are dispensed at a temperature at which the topping type is considered to taste "better." Furthermore, because the automated foodstuff assembly apparatus (actively or passively) heats toppings samples in the hopper to temperatures greater than the low threshold temperature, the automated foodstuff assembly apparatus can also implement methods and techniques described above to track temperatures of topping samples (e.g., or topping sample segments, clusters of topping samples, etc.) over time, to set timers for topping samples exposed to temperatures greater than the threshold low temperature, and to discard or otherwise mark for disposal topping samples associated with expired timers.

14.1 Demand Prediction

In one implementation, the automated foodstuff assembly apparatus manipulates temperatures of a hopper loaded into the topping module based on current or predicted upcoming demand for a topping type loaded into and dispensed from the hopper, as shown in FIG. 5.

In one example, the topping module receives a hopper containing a column of tomatoes—with the top and the bottom of each tomato in the column of tomatoes removed—in Block S110. In this example, the topping module can include a temperature control system, such as separate heating and cooling systems or an integrated heating/cooling system (e.g., a thermoelectric cooler). In Block S170, the automated foodstuff assembly apparatus can initially set the temperature control system to cool and maintain the column of tomatoes in the hopper below a low threshold temperature (e.g., 41° Fahrenheit) during a first period of time. Later, when the current or anticipated upcoming demand for tomatoes at the automated foodstuff assembly apparatus reaches a level sufficient to yield consumption of all or at least a threshold fraction (e.g., 90%) of tomatoes stored in the hopper within the preset duration of an over-temperature timer (e.g., within four hours), the automated foodstuff assembly apparatus can set the temperature control system to raise the temperature of tomatoes in the hopper to a more preferred serving temperature. In particular, in Block S172, the automated foodstuff assembly apparatus can set the temperature control system to raise and maintain a remaining portion of the column of tomatoes in the hopper at a target consumption temperature (e.g., 55° F. (12.8° C.)). (In Block S172, the automated foodstuff assembly apparatus can similarly set the temperature control system to maintain remaining tomatoes in the hopper within a target consumption temperature range or bound, such as between 51° F. (10.5° C.) and 60° F. (15.5° C.)). Once the temperature of a tomato in the hopper rises above the low threshold temperature, the automated foodstuff assembly apparatus can set a timer for the tomato (or for a corresponding cluster of tomatoes, for the entire column of tomatoes in the hopper, etc.) in Block S120 and later flag the tomato for disposal in Block S160 if the tomato remains in the hopper after expiration of the timer.

The automated foodstuff assembly apparatus can therefore maintain temperatures of topping samples in the topping module below a low threshold temperature in Block S170 while current or predicted upcoming demand remains below a demand threshold, and the automated foodstuff assembly apparatus can elevate temperatures of topping samples in the topping module to a preferred consumption temperature in Block S172 when current or predicted upcoming demand for the topping type exceeds the demand threshold.

In the implementation, the automated foodstuff assembly apparatus (or a local or remote computer system in communication with the automated foodstuff assembly apparatus) can implement a static demand threshold. For example, for a hopper configured to contain ten tomatoes cut to 2.5" in height installed in a topping module configured to cut and dispense tomato slices 0.3" in thickness and for a timer duration of four hours following an over-temperature event, the automated foodstuff assembly apparatus can implement a static demand threshold of 21 tomato slices per hour, which corresponds to complete exhaustion of tomato slices from the hopper within four hours if tomato is specified in no fewer than 21 food orders fulfilled by the automated foodstuff assembly apparatus per hour. In a similar example, the automated foodstuff assembly apparatus can implement a static demand threshold of 18 tomato slices per hour, which corresponds to 85% exhaustion of a full hopper within four hours if tomato is specified in no fewer than 21 food orders fulfilled by the automated foodstuff assembly apparatus per hour.

Alternatively, the automated foodstuff assembly apparatus (or the local or remote computer system) can calculate and implement a dynamic demand threshold based on an amount of topping samples remaining in the hopper and/or based on a target yield from the hopper. For example, the automated foodstuff assembly apparatus can track a height of tomatoes in the hopper in Block S150, as described above, translate the height of tomatoes into an amount of tomatoes left in the hopper, and then calculate a minimum demand threshold to fully exhaust the remaining stack of tomatoes (i.e., 100%) within the preset timer duration (e.g., four hours). As in the foregoing example, to achieve 100% yield from the hopper, the automated foodstuff assembly apparatus: can calculate a demand threshold of 21 tomato slices per hour when the stack of tomatoes is 25" tall; can calculate a demand threshold of 15 tomato slices per hour when the stack of tomatoes is 18" tall; and can calculate a demand threshold of 5 tomato slices per hour when the stack of tomatoes is 6" tall. The automated foodstuff assembly apparatus can also vary the target yield over time, such as by setting a high target yield (e.g., ~100%) when a restaurant housing the automated foodstuff assembly apparatus opens and by lowering the target yield (e.g., down to 50%) as the restaurant nears a closing time. As in the foregoing example, the automated foodstuff assembly apparatus: can calculate a demand threshold of 21 tomato slices per hour to achieve a yield of 100% when the stack of tomatoes is 25" tall at startup at 10 AM; can calculate a demand threshold of 13.5 tomato slices per hour to achieve a yield of 90% when the stack of tomatoes is 18" tall at 12 PM; and can calculate a demand threshold of 5 tomato slices per hour to achieve a yield of 50% when the stack of tomatoes is 6" tall at 9 PM, two hours before closing. However, the automated foodstuff assembly apparatus can implement a static demand threshold of any other value or can calculate a dynamic demand threshold in any other way and according to any other parameter.

The automated foodstuff assembly apparatus (or the remote computer system) can calculate a current demand for the topping type loaded into the topping module from food orders—in a queue assigned to the automated foodstuff assembly apparatus—specifying the topping type and/or from food orders specifying the topping type and recently fulfilled by the automated foodstuff assembly apparatus. The automated foodstuff assembly apparatus can also predict upcoming or future demand for the topping type at the automated foodstuff assembly apparatus based on historic demand for the topping type, such as based on food orders in past queues assigned to the automated foodstuff assembly apparatus. For example, throughout operation of the automated foodstuff assembly apparatus, a remote computer system can retrieve queues of food orders previously assigned to and fulfilled by the automated foodstuff assembly apparatus, identify a subset of food orders specifying the topping type loaded into the topping module in the previous queues, and predict demand for the topping type over a subsequent period of time (e.g., a subsequent four-hour period) based on the number of food orders—specifying the topping type—submitted by patrons over a similar period of time on similar days (e.g., the same four-hour block over the last five weekdays, over the last three Fridays, or on the last Sunday). The computer system can then compare this historic demand for the topping type to the demand threshold described above; if the historic demand exceeds the demand threshold, the computer system can prompt the automated foodstuff assembly apparatus to elevate the temperature of the hopper to a target consumption temperature (or target consumption temperature range). The automated foodstuff assembly apparatus can then raise the temperature of the hopper in Block S172, track temperatures of the topping samples in Block S110, and set timers for the topping samples in Block S120 accordingly.

However, the automated foodstuff assembly apparatus and/or the computer system can implement any other method or technique to anticipate an increase in demand during a subsequent period of time.

14.2 Temperature Control

In this variation, the topping module can include a temperature control system. For example, the topping module can include discrete heating and cooling systems or an integrated heating and cooling system arranged along the receiver and configured to actively heat and cool the length of the hopper. In this example, the temperature control system can be fixed within the topping module.

In the implementation in which the topping module includes a magazine configured to store multiple hoppers, the automated foodstuff assembly apparatus temperature control system can heat and cool multiple hoppers in the topping module, such as including a hopper in the discharge position and hoppers in secondary positions behind the discharge position, as shown in FIGS. 5 and 6. In this implementation, because temperatures across the hoppers may be substantially uniform and dependent, the automated foodstuff assembly apparatus (or the remote computer system) can calculate a demand threshold for the topping module based on a total amount of topping samples across multiple hoppers in the topping module.

Alternatively, in the implementation in which the topping module includes a magazine configured to store multiple hoppers, the topping module can include multiple temperature control systems, including one temperature control system integrated into each receptacle within the magazine, and the automated foodstuff assembly apparatus can independently set the temperature of each temperature control system to independently control the temperature of each hopper. Alternatively, the topping module can include a first temperature control system configured to control a temperature of a hopper in the discharge position and a second temperature control system configured to control temperatures of the hopper in the secondary position behind the discharge position independent of the first temperature control system. The automated foodstuff assembly apparatus can thus control the first temperature control system to increase the temperature of a hopper in the discharge position to a target consumption temperature in Block S172 while maintaining temperatures of other hoppers in the magazine below the low temperature threshold. For example, in Block S170, the automated foodstuff assembly apparatus can maintain both a first hopper in the discharge position and a second hopper in a secondary position behind the discharge position below the low threshold temperature. In this example, the automated foodstuff assembly apparatus can later increase the temperature of the first hopper to the target consumption temperature in Block S172 while maintaining the second hopper below the low threshold temperature.

Yet alternatively, the temperature control system can be integrated into the hopper, such as in the form of a thermoelectric cooler independently powered by an integrated battery or by the topping module via an electrical junction in the receiver or in the magazine.

In another implementation in which the automated foodstuff assembly apparatus includes multiple topping modules, the automated foodstuff assembly apparatus can include a manifold thermally coupled to each topping module and to the temperature control system, and the temperature control system can actively heat and/or cool hoppers in each topping module via the manifold. For example, the topping module can include a blower that recirculates heated or cooled air from the temperature control system, through the manifold, around the topping modules, and back to the temperature control system. In this implementation, the automated foodstuff assembly apparatus can manipulate the output of the temperature control system to control temperatures of hoppers across multiple topping modules. The automated foodstuff assembly apparatus (or the remote computer system) can thus calculate a demand threshold and set a target temperature for the topping modules based on amounts of topping samples and predicted aggregate demand for topping types dispensed from the topping modules.

Yet alternatively, the temperature control system can be configured to induce a temperature gradient along the height of the hopper, such as a temperature within the target consumption temperature proximal a discharge end of the hopper and a temperature below the low threshold temperature proximal the top of the hopper. The automated foodstuff assembly apparatus can thus selectively elevate temperatures of a subset of topping samples in the hopper (i.e., topping samples near the discharge end of the hopper) up to or near the target consumption temperature while maintaining other topping samples below or near the low threshold temperature. In this implementation, the automated foodstuff assembly apparatus can calculate a demand threshold to trigger elevation of the temperature of one or more topping samples in the hopper based on a temperature gradient induced by the temperature control system (e.g., a number of topping samples in the hopper elevated to a temperature above the low threshold temperature when a lowest topping sample in contact with the blade is heated to a temperature within the target consumption temperature range). In this implementation, the automated foodstuff assembly apparatus can also track the temperature of each topping sample (or each topping sample segment, cluster of topping samples, etc.) in the hopper in Block S120.

However, in this variation, the topping module and the automated foodstuff assembly apparatus can include any other one or more temperature control systems arranged in any other way to heat and/or cool topping samples in one or more hoppers.

15. Temperature Exposure

As shown in FIG. 7, one variation of the method includes: at a first time, measuring a first temperature at a first position within a hopper containing a series of topping samples of a topping type; substantially at the first time, measuring a first temperature at a second position within the hopper above the first position; estimating a temperature of each topping sample in the series of topping samples in the hopper at the first time based on the first temperature at the first position, the first temperature at the second position, and a first position of each topping sample in the series of topping samples in the hopper at the first time in Block S120; at a second time succeeding the first time, in response to dispensing a slice of a first topping sample in the series of topping samples from the hopper onto a topping vehicle arranged below the hopper, determining a second position of each topping sample in the series of topping samples within the hopper in Block S150; substantially at the second time, measuring a second temperature at the first position within the hopper; substantially at the second time, measuring a second temperature at the second position within the hopper; estimating a temperature of each topping sample in the series of topping samples in the hopper at the second time based on the second temperature at the first position, the second temperature at the second position, and the second position of each topping sample in the series of topping samples in the hopper in Block S120; calculating a temperature exposure of each topping sample in the series of topping samples up to the second time based on the temperatures of topping samples in the series of topping samples in the hopper at the first time and at the second time in Block S180; and, in response to a temperature exposure of a particular topping sample in the series of topping samples exceeding a threshold temperature exposure prior to dispensation of a final portion of the particular topping sample from the hopper, discarding the final portion of the particular topping sample from hopper in Block S160.

As shown in FIG. 7, a similar variation of the method includes: at a first time, measuring a first temperature within a hopper containing a series of topping samples of a topping type; at a second time succeeding the first time, measuring a second temperature within the hopper; for a particular topping sample, in the series of topping samples, in a dispense position within the hopper, estimating a temperature exposure of the particular topping sample based on the first temperature, the second temperature, and a duration between the first time and the second time in Block S120; in response to the temperature exposure of the particular topping sample exceeding a threshold temperature exposure, discarding the particular topping sample from the hopper in Block S160; and, based on a request for a slice of the topping type for a topping vehicle adjacent the topping module, in response to the threshold temperature exposure exceeding the threshold temperature exposure of the particular topping sample, dispensing a slice of the particular topping sample, from the hopper, onto the topping vehicle in Block S140.

Generally, in this variation, the automated foodstuff assembly apparatus can integrate determined temperatures of a topping sample stored in the hopper over time, such as from a time that the topping sample is loaded into the hopper, in order to calculate a "volume" of heat exposure of the topping sample. (The automated foodstuff assembly apparatus can similarly calculate a volume of heat exposure of a segment of a topping sample, a column of topping samples, etc. stored in the hopper.) The automated foodstuff assembly apparatus can maintain and update a value of temperature exposure of a topping sample stored in the hopper. Throughout operation, the automated foodstuff assembly apparatus can compare this temperature exposure value for the topping sample—such as after each sampling period and/or when a slice is about to be cut from the topping sample and dispensed onto a topping vehicle—to a threshold heat exposure value to confirm that the slice of the topping sample has not been exposed to excess heat. In this variation, the automated foodstuff assembly apparatus can implement a threshold heat exposure value corresponding to a maximum allowable heat exposure before expiration of a topping sample, and the automated foodstuff assembly apparatus can thus disqualify a topping sample once the determined heat exposure of the topping sample exceeds the threshold heat exposure value. Alternatively, the automated foodstuff assembly apparatus can implement a threshold heat exposure value corresponding to a timer trigger, and the automated foodstuff assembly apparatus can thus set a timer for a topping sample once the determined heat exposure of the topping sample exceeds the threshold heat exposure value.

15. Condiments

In one implementation, the automated foodstuff assembly apparatus also includes one or more condiment containers containing volumes of condiments, such as relish, ketchup, mustard, barbecue sauce, salsa, hot sauce, etc. In this implementation, the automated foodstuff assembly apparatus can execute Blocks of the method to track temperatures (or heat exposures) of a volume of condiment stored in a condiment container, to set a timer for the volume of condiment stored in the condiment container in response to temperature of the condiment exceeding a threshold temperature, and to selectively dispense and discard condiment from the condiment container based on the state of the timer, as described above.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

I claim:

1. A method for handling foodstuffs according to temperature exposure within an automated foodstuff assembly apparatus, the method comprising:
    at a topping module, receiving a hopper carrying a plurality of topping samples arranged from a first end of the hopper toward an opposite end of the hopper;
    monitoring a plurality of temperatures corresponding one-to-one with the plurality of topping samples, wherein the monitoring includes making a plurality of first temperature measurements corresponding to one of the plurality of topping samples and making a plurality of second temperature measurements corresponding to another one of the plurality of topping samples; and
    electronically maintaining a set of timers, wherein the electronically maintaining includes:
        in response to any one of the plurality of temperatures exceeding a threshold temperature, (i) assigning a timer of the set of timers to the topping sample corresponding to the temperature that exceeds the threshold temperature and (ii) starting the assigned timer at a predetermined time; and
        in response to expiration of any one of the set of timers:
            identifying which of the plurality of topping samples the expired timer was assigned to,
            determining whether a final portion of the identified topping sample has been dispensed from the topping module, and
            preventing dispensation of the final portion of the identified topping sample onto a topping vehicle.

2. The method of claim 1, wherein:
preventing dispensation of the final portion of the identified topping sample comprises:
    moving the hopper from a dispense position to a discard position; and
the method further comprises:
    moving another hopper carrying another plurality of topping samples from a secondary position to the dispense position.

3. The method of claim 1, wherein preventing dispensation of the final portion of the identified topping sample onto the topping vehicle includes:
    extending a discard chute under a blade of the topping module; and
    actuating the blade to dispense slices of the final portion of the identified topping sample onto the discard chute until the final portion of the identified topping sample is exhausted from the topping module.

4. The method of claim 3, wherein preventing dispensation of the final portion of the identified topping sample onto the topping vehicle further comprises draining fluid discharged by the final portion of the identified topping sample from the topping module and disinfecting the blade.

5. The method of claim 1, wherein preventing dispensation of the final portion of the identified topping sample onto the topping vehicle comprises ceasing operation of the topping module and issuing a flag for manual removal of the hopper from the topping module.

6. The method of claim 5,
further comprising:
receiving food orders from patrons over time;
inserting food orders into a first queue assigned to the automated foodstuff assembly apparatus and into a second queue assigned to another automated foodstuff assembly apparatus; and
dispensing servings of topping samples from the topping module onto topping vehicles based on food orders in the first queue;
wherein preventing dispensation of the final portion of the identified topping sample onto the topping vehicle comprises:
distributing a first subset of food orders stored in the first queue to the second queue, wherein the first subset of food orders specifies inclusion of a first topping type, and wherein the plurality of topping samples are of the first topping type; and
distributing a second subset of food orders stored in the second queue to the first queue, wherein the second subset of food orders specifies exclusion of the first topping type.

7. The method of claim 1, further comprising:
maintaining the first end of the hopper within a consumption temperature range greater than the threshold temperature; and
maintaining the opposite end of the hopper within a low temperature range less than the threshold temperature.

8. The method of claim 1, further comprising:
interpolating a temperature of each of a plurality of sections of each topping sample based on the first temperature measurements, the second temperature measurements, and a section thickness.

9. The method of claim 1, wherein making the first and second temperature measurements comprises:
determining a height of a column of the topping samples in the topping module;
scanning the column of topping samples with a contactless temperature sensor; and
mapping a column of position-based temperature values output by the contactless temperature sensor to the height of the column of topping samples.

10. The method of claim 1, wherein preventing dispensation of the final portion of the identified topping sample includes discarding the final portion of the identified topping sample.

11. A method for handling foodstuffs according to temperature exposure within an automated foodstuff assembly apparatus, the method comprising:
at a topping module, receiving a hopper containing a plurality of topping samples of a first topping type;
during a first period of time:
maintaining the topping samples within a first temperature range less than a low threshold temperature;
sequentially cutting slices from at least one of the topping samples; and
dispensing the slices onto topping vehicles;
acquiring historical demand data, wherein:
the historical demand data includes numbers of historical foodstuff orders that include the first topping type, and
the historical demand data includes days of week and times of day at which each of the historical foodstuff orders were fulfilled by the automated foodstuff assembly apparatus;
predicting an increase in demand for the first topping type based on the historical demand data;
in response to determination of the increase in demand for the first topping type, beginning a transition period of time following the first period of time during which temperatures of a remaining portion of the topping samples are increased from the first temperature range to a target consumption temperature range that is greater than the low threshold temperature;
during a second period of time succeeding the transition period of time:
maintaining the remaining portion of the topping samples within the target consumption temperature range;
setting a timer for the remaining portion of the topping samples;
prior to expiration of the timer:
sequentially cutting slices from the remaining portion of the topping samples; and
dispensing the slices cut from the remaining portion of the topping samples onto topping vehicles; and
in response to expiration of the timer prior to dispensation of a final portion of the remaining portion of the topping samples, preventing dispensation of the final portion of the remaining portion of the topping samples onto a topping vehicle.

12. The method of claim 11, further comprising heating the hopper from a first temperature within the first temperature range to a second temperature within the target consumption temperature range during the transition period of time.

13. The method of claim 11,
wherein preventing dispensation of the final portion of the remaining portion of the topping samples onto the topping vehicle comprises:
moving the hopper from a dispense position to a discard position; and
wherein the method further comprises moving another hopper from a secondary position to the dispense position.

14. The method of claim 13, wherein:
maintaining the topping samples within the first temperature range during the first period of time comprises maintaining the hopper within the first temperature range; and
maintaining the topping samples within the target consumption temperature range during the second period of time comprises maintaining the hopper within the target consumption temperature range.

15. The method of claim 11, wherein preventing dispensation of the final portion of the remaining portion of the topping samples onto the topping vehicle comprises ceasing operation of the topping module and issuing a flag for manual removal of the hopper from the topping module.

16. The method of claim 11, further comprising, in response to expiration of the timer, extending a drip tray under the topping module.

* * * * *